US008697354B2

(12) United States Patent
Ebright

(10) Patent No.: US 8,697,354 B2
(45) Date of Patent: Apr. 15, 2014

(54) RNA-EXIT-CHANNEL: TARGET AND METHOD FOR INHIBITION OF BACTERIAL RNA POLYMERASE

(76) Inventor: Richard H. Ebright, North Brunswick, NJ (US)

( * ) Notice: Subject to any disclaimer, the term of this patent is extended or adjusted under 35 U.S.C. 154(b) by 0 days.

(21) Appl. No.: 13/474,255

(22) Filed: May 17, 2012

(65) Prior Publication Data

US 2012/0322056 A1  Dec. 20, 2012

Related U.S. Application Data

(62) Division of application No. 10/527,559, filed as application No. PCT/US2004/016826 on May 28, 2004, now Pat. No. 8,206,898.

(60) Provisional application No. 60/473,485, filed on May 28, 2003.

(51) Int. Cl.
*C12Q 1/70* (2006.01)
*G01N 33/53* (2006.01)

(52) U.S. Cl.
USPC .................................. 435/5; 435/7.9; 435/34

(58) Field of Classification Search
None
See application file for complete search history.

(56) References Cited

U.S. PATENT DOCUMENTS

| 5,919,666 | A | 7/1999 | Young et al. |
| 6,225,076 | B1 | 5/2001 | Darst et al. |
| 2002/0034808 | A1 | 3/2002 | Darst et al. |
| 2003/0003481 | A1 | 1/2003 | Landick et al. |
| 2003/0232369 | A1 | 12/2003 | Bushnell |

OTHER PUBLICATIONS

Sonenshein et al., J. Bacteriol., 132, 1, 73-79, 1977.
Sergio et al., J. Antibiot., 28, 7, 543-549, 1975.
Talpaert et al., Bioch. Biophy Res. Comm., 63, 1, 328-334, 1975.
International Search Report and Written Opinion from the ISA, dated Mar. 24, 2005, issued in connection with corresponding International Application No. PCT/US04/16826.
Binder, et al.; Emerging Infectious Diseases: Public Health Issues for the 21st Century; Science; vol. 284, pp. 1311-1313; May 21, 1999.
Blond, et al.; The Cyclic Structure of Microcin J25, a 21-Residue Peptide Antibiotic from *Escherichia coli*; Eur. J. Biochem.; vol. 259; pp. 747-755; (1991).
Blondelle, et al.; Identification of Antimicrobial Peptides by Using Combinatorial Libraries Made Up of Unnatural Amino Acids; Antimicrobial Agents and Chemotherapy; vol. 38, No. 10; pp. 2280-2286; Oct. 1994.
Blondelle, et al.; The Antimicrobial Activity of Hexapeptides Derived from Synthetic Combinatorial Libraries; Journal of Applied Bacteriology; vol. 78; pp. 39-46; (1995).
Bushnell, et al.; Structural Basis of Transcripton: x-Amanitin-RNA Polymerase II Cocrystal at 2.8 ÅResolution, PNAS; vol. 99, No. 3; pp. 1218-1222; Feb. 5, 2002.

Campbell, et al.; Structural Mechanism for Rifampicin Inhibition of Bacterial RNA Polymerase; Cell; vol. 104, No. 6; pp. 901-912; Mar. 23, 2001.
Cech, et al.; Characterization of Ribonucleic Acid Polymerase-T7 Promoter Binary Complexes; Biochemistry; vol. 19; pp. 2440-2447; May 27, 1980.
Christie, et al.; *Escherichia coli* rpoC397 Encodes a Temperature-Sensitive C-Terminal Frameshift in the B' Subunit of RNA Polymerase That Blocks Growth of Bacteriophage P2; Journal of Bacteriology; vol. 178, No. 23; pp. 6991-6993; Dec. 1996.
Zhang, et al.; Crystal Structure of *Thermus aquaticus* Core RNA Polymerase at 3.3 Å Resolution; Cell; vol. 98; pp. 811-824; (1999).
Christopher Walsh; Molecular Mechanisms That Confer Antibacterial Drug Reisstance: Nature, vol. 406; pp. 775-781; Aug. 17, 2000.
Cramer, et al.; Architecture of RNA Polymerase II and Implications for the Transcription Mechanism; Science; vol. 288, No. 5466; pp. 640-649; Apr. 28, 2000.
Cwirla, et al.; Peptides on Phage: A Vast Library of Peptides for Identifying Ligands; Proceedings of the National Academy of Sciences; vol. 87, No. 16; pp. 6378-6382; Aug. 1990.
D. A. Mitchison; Role of Individual Drugs in the Chemotherapy of Tuberculosis; International Journal of Tuberculosis and Lung Disease; 4(9); pp. 796-806; (2000).
Delgado, et al.; *Escherichia coli* RNA Polymerase is the Target of the Cyclopeptide Antibiotic Microcin J25; Journal of Bacteriology; vol. 183, No. 15; pp. 4543-4550; Aug. 2001.
Zhou, et al; Identification of the Activating Region of Catabolite Gene Activator Protein (CAP): Isolation and Characterization of Mutants of CAP Specifically Defective in Transcription Activation; Proc. Natl. Acad. Sci. USA; pp. 6081-6085; Jul. 1993 Biochemistry.
Devlin, et al; Random Peptide Libraries: A Source of Specific Protein Binding Molecules; Science; vol. 249; pp. 404-406; Jul. 27, 1990.
Epshtein, et al.; Swing-Gate Model of Nucleotide Entry into the RNA Polymerase Active Center; Molecular Cell; vol. 10, No. 3; pp. 623-634; Sep. 2002.
Felici, et al.; Selection of Antibody Ligands from a Large Library of Oligopeptides Expressed on a Multivalent Exposition Vector; J. Mol. Biol.; vol. 222, No. 2; pp. 301-310; (1991).
Gallop, et al; Applications of Combinatorial Technologies to Drug Discovery. I. Background and Peptide Combinatorial Libraries; Journal of Medicinal Chemistry; vol. 37, No. 9; pp. 1233-1251; Apr. 29, 1994.
Geysen, et al.; The Delineation of Peptides Able to Mimic Assembled Epitopes; pp. 130-149.

(Continued)

*Primary Examiner* — Nancy T Vogel
(74) *Attorney, Agent, or Firm* — Davidson, Davidson & Kappel, LLC

(57) ABSTRACT

The invention provides a target and methods for specific binding and inhibition of RNAP from bacterial species. The invention is directed to a method for identifying agents that bind to a bacterial RNAP homologous RNA-exit-channel amino-acid sequence, comprising preparing a reaction solution comprising the agent to be tested and an entity comprising a bacterial RNAP homologous RNA-exit-channel amino-acid sequence, and detecting presence or amount of binding. The invention has applications in control of bacterial gene expression, control of bacterial growth, antibacterial chemistry, and antibacterial therapy.

31 Claims, 3 Drawing Sheets

(56) References Cited

OTHER PUBLICATIONS

Gill, et al.; Calculation of Protein Extinction Coefficients from Amino Acid Sequence Data; Analytical Biochemistry; vol. 182; pp. 319-326; (1989).

Gill, et al.; *Escherichia coli* s70 and NusA Proteins: I. Binding Interactions With Core RNA Polymerase in Solution and Within the Transcription Complex; J. Mol. Biol.; vol. 220, No. 2; pp. 307-324; (1991).

Gnatt, et al.; Structural Basis of Transcription: An RNA Polymerase II Elongation Complex at 3.3 Resolution; Science; vol. 292; pp. 1876-1881; Jun. 8, 2001.

Houghten, et al.; Generation and Use of Synthetic Peptide Combinatorial Libraries for Basic Research and Drug Discovery; Nature; vol. 354, No. 6348; pp. 84-86; Nov. 7, 1991.

Houghten, et al.; The Use of Synthetic Peptide Combinatorial Libraries for the Identification of Bioactive Peptides; BioTechniques; vol. 13, No. 3; pp. 412-421; (1992).

Kim et al.; Mechanism of ATP-Dependent Promoter Melting by Transcription Factor IIH; Science; vol. 288, No. 5470; pp. 1418-1421; May 26, 2000.

Korzheva, et al.; A Structural Model of Transcription Elongation; Science; vol. 289; pp. 619-625; Jul. 28, 2000.

Lam, et al.; A New Type of Synthetic Peptide Library for Identifying Ligand-Binding Activity; Nature; vol. 354, pp. 82-84; Nov. 7, 1991.

Luzzago, et al; Mimicking of Discontinuous Epitopes by Phage-Displayed Peptides, I. Epitope Mapping of Human H Ferritin Using a Phage Library of Constrained Peptides; Gene, 128; pp. 51-57; (1993).

McConnell, et al.; Constrained Peptide Libraries as a Tool for Finding Mimotopes; Gene; vol. 151, Nos. 1 and 2; pp. 115-118; (1994).

McLafferty, et al; M13 Bacteriophage Displaying Disulfide-Constrained Microproteins; Gene, 128 ; pp. 29-36; (1993).

Mekler, et al.; Structural Organization of Bacterial RNA Polymerase Holoenzyme and the RNA Polymerase-Promoter Open Complex; Cell; vol. 108, No. 5; pp. 599-614; Mar. 8, 2002.

Mukhopadhyay, et al.; Translocation of sigma70 with RNA Polymerase During Transcription: Fluorescence Resonance Energy Transfer Assay for Movement Relative to DNA; Cell; vol. 106; pp. 453-463; Aug. 24, 2001.

Zhou, et al.; Random Mutagenesis of Gene-sized DNA Molecules by Use of PCR with Taq DNA Polymerase; Nucleic Acids Research; vol. 19, No. 21; p. 6052; (1991).

Murakami, et al.; Structural Basis of Transcription Initiation: An RNA Polymerase Holoenzyme-DNA Complex; Science; vol. 296; pp. 1285-1290; May 17, 2002.

N. W. Schluger; The Impact of Drug Resistance on the Global Tuberculosis Epidemic; International Journal of Tuberculosis and Lung Disease; 4(2); pp. 571-575; 2000.

Naryshkin, et al.; Structural Organization of the RNA Polymerase-Promoter Open Complex; Cell; vol. 101, No. 6; pp. 601-611; Jun. 9, 2000.

Niu, et al.; Transcription Activation at Class II CAP-Dependent Promoters: Two Interactions Between CAP and RNA Polymerase; Cell; vol. 87, No. 6; pp. 1123-1134; Dec. 13, 1996.

Ostresh, et al.; Generation and Use of Nonsupport-Bound Peptide and Peptidomimetic Combinatorial Libraries; Methods in Enzymology; vol. 267; pp. 220-234; (1996).

Ostresh, et al.; Libraries from Libraries: Chemical Transformation of Combinatorial Libraries to Extend the Range and Repertoire of Chemical Diversity; Proc. Natl. Acad. Sci. USA; vol. 91; pp. 11138-11142; Nov. 1994 Chemistry.

Ostresh, et al.; Peptide Libraries: Determination of Relative Reaction Rates of Protected Amino Acids in Competitive Couplings; Biopolymers; vol. 34, No. 12; pp. 1681-1689; Dec. 1994.

Perez-Paya, et al; Soluble Combinatorial Libraries of Organic, Peptidomimetic and Peptide Diversities; Trends in Analytical Chemistry; vol. 14, No. 2; pp. 83-92; (1995).

Permley, et al.; Antibody-Selectable Filamentous fd Phage Vectors: Affinity Purification of Target Genes; Gene; vol. 73; pp. 305-318; (1988).

Pinilla, et al.; A Review of the Utility of Soluble Peptide Combinatorial Libraries; Biopolymers (Peptide Science); vol. 37; pp. 221-240; (1995).

Pinilla, et al.; Rapid Identification of High Affinity Peptide Ligands Using Positional Scanning Synthetic Peptide Combinatorial Libraries; BioTechniques; vol. 13, No. 6; pp. 901-905; Dec. 1992.

Pinilla, et al; Versatility of Positional Scanning Synthetic Combinatorial Libraries for the Identification of Individual Compounds; Drug Development Research 33; pp. 133-145; (1994).

Raviglione, et al.; The Burden of Drug-Resistant Tuberculosis and Mechanisms for Its Control; Annals of the New York Academy of Sciences; vol. 953; pp. 88-97; (2001).

Richard A. Houghten; General Method for the Rapid Solid-Phase Synthesis of Large Numbers of Peptides: Specificity of Antigen-Antibody Interaction at the Level of Individual Amino Acids; Proc. Natl. Acad. Sci. USA; vol. 82; pp. 5131-5135; Aug. 1985 Immunology.

Richard H. Ebright; RNA Polymerase: Structural Similarities Between Bacterial RNA Polymerase and Eukaryotic RNA Polymerase II; J. Mol. Biol.; vol. 304, No. 5; pp. 687-698; (2000).

Scott, et al.; Searching for Peptide Ligands With an Epitope Library; Science; vol. 249; pp. 386-390; Jul. 27, 1990.

Solbiati, et al.; Genetic Analysis of Plasmid Determinants for Microcin J25 Production and Immunity; Journal of Bacteriology; vol. 178, No. 12; pp. 3661-3663; Jun. 1996.

Solbiati, et al.; Sequence Analysis of the Four Plasmid Genes Required to Produce the Circular Peptide Antibiotic Microcin J25; Journal of Bacteriology; vol. 181, No. 8; pp. 2659-2662; Apr. 1999.

Stuart B. Levy; The Challenge of Antibiotic Resistance; Scientific American; vol. 278, No. 3; pp. 46-53; Mar. 1998.

Vassylyev, et al.;Crystal Structure of a bacterial RNA Polymerase Holoenzyme at 2.6 Resolution; Nature; pp. 712-719; Jun. 2002.

Wang, et al.; Discontinuous Movements of DNA and RNA in RNA Polymerase Accompany Formation of a Paused Transcription Complex; Cell; vol. 81, No. 3; pp. 341-350; May 5, 1995.

Yuzenkova, et al.; Mutations of Bacterial RNA Polymerase Leading to Resistance to Microcin J25; Journal of Biological Chemistry; vol. 277, No. 52; pp. 50867-50875; Dec. 27, 2002.

FIG. 1A

```
RPOC_ECOLI  (243)  PVLPPDLRPLV
RPOC_HAEIN  (244)  PVLPPDLRPLV
RPOC_VIBCH  (243)  PVLPPDLRPLV
RPOC_PSEAE  (243)  PVLPPDLRPLV
RPOC_TREPA  (232)  PVIPPDLRPMV
RPOC_BORBU  (232)  PVIPPEIRPMV
RPOC_XYLFA  (266)  PVLPPDLRPLV
RPOC_CAMJE  (265)  PVLPPDLRPLV
RPOC_NEIMA  (245)  PVLPPDLRPLV
RPOC_RICPR  (243)  PVIPPEIRPLV   ⎫
RPOC_CHLTR  (246)  PVMPPDLRPLV   ⎬ BACTERIAL RNA POLYMERASE
RPOC_MYCPN  (303)  PVIPPDIRPII   ⎭
RPOC_BACSU  (232)  PVIPPELRPMV
RPOC_STAAU  (232)  PIIPPEIRPMA
RPOC_MYCTU  (318)  PVIPPELRPMV
RPOC_SYNY3  (250)  PVIPPDLRPMV
RPOC_AQUAE  (374)  PVLPPELRPLV
RPOC_DEIRA  (535)  PVMPPDLRPMV
RPOC_TTHER  (518)  PVLPPDLRPMV
RPOC_THEAQ  (518)  PVLPPDLRPMV
RPA1_HUMAN  (303)  VVPPSGRPVS    ⎫
RPB1_HUMAN  (254)  PVPPLSVRPAV   ⎬ HUMAN RNA POLYMERASES I, II, III
RPC1_HUMAN  (256)  LVPPLCFRPSV   ⎭
```

FIG. 1B

| | 1251 (E.C.) | 1256 (E.C.) | | 1321 (E.C.) | |
|---|---|---|---|---|---|
| RPOB_ECOLI (1249) | GSNSLVTDP | (1320) | PESFNV | |
| RPOB_HAEIN (1250) | GSNSLVTDP | (1321) | PESFNV | |
| RPOB_VIBCH (1282) | GSNSLVTDP | (1353) | PESFNV | |
| RPOB_PSEAE (1254) | GSNSLVTDP | (1335) | PESFNV | |
| RPOB_TREPA (1063) | GPNSLVTDP | (1134) | PESFNV | |
| RPOB_BORBU (1044) | GPNSLVTDP | (1115) | PESFNV | |
| RPOB_XYLFA (1295) | GPNSLVTDP | (1366) | PESFNV | |
| RPOB_CAMJE (1280) | GPNSLVTDP | (1351) | PEIFFV | |
| RPOB_NEIMA (1299) | GPNSLVTDP | (1370) | PESFNV | |
| RPOB_RICPR (1278) | GPNSLVTDP | (1349) | PESFNV | BACTERIAL RNA POLYMERASE |
| RPOB_CHLTR (1157) | GPNSLVTDP | (1228) | PESFNV | |
| RPOB_MYCPN (1265) | GPNSKITDP | (1336) | PESFKL | |
| RPOB_BACSU (1054) | GPNSLVTDP | (1125) | PESFKV | |
| RPOB_STAAU (1055) | GPNSLVTDP | (1126) | PESFRV | |
| RPOB_MYCTU (1047) | GPNSMITDP | (1118) | PESFKV | |
| RPOB_SYNY3 (966) | GPNSLVTDP | (1037) | PESFKV | |
| RPOB_AQUAE (1359) | GPNSLVTDP | (1430) | PESFKV | |
| RPOB_DEIRA (1071) | GPNSLITDP | (1142) | PESFKV | |
| RPOB_TTHER (1011) | GPNSLITDP | (1082) | PESFRV | |
| RPOB_THEAQ (1011) | GPNSLITDP | (1082) | PESFRV | |
| RPA2_HUMAN (960) | GANDNVTDP | (1057) | PIVFAY | |
| RPB2_HUMAN (1065) | GPIDTLNTDP | (1152) | PMACKL | HUMAN RNA POLYMERASES I, II, III |
| RPC2_HUMAN (1026) | GPNAVLTDP | (1107) | PMACKL | |

SEQUENCE LISTING

<160> NUMBER OF SEQ ID NOS: 69

<210> SEQ ID NO 1

-continued

```
<211> LENGTH: 11
<212> TYPE: PRT
<213> ORGANISM: Escherichia coli

<400> SEQUENCE: 1

Pro Val Leu Pro Pro Asp Leu Arg Pro Leu Val
1               5                   10

<210> SEQ ID NO 2
<211> LENGTH: 11
<212> TYPE: PRT
<213> ORGANISM: Haemophilus influenzae

<400> SEQUENCE: 2

Pro Val Leu Pro Pro Asp Leu Arg Pro Leu Val
1               5                   10

<210> SEQ ID NO 3
<211> LENGTH: 11
<212> TYPE: PRT
<213> ORGANISM: Vibrio cholerae

<400> SEQUENCE: 3

Pro Val Leu Pro Pro Asp Leu Arg Pro Leu Val
1               5                   10

<210> SEQ ID NO 4
<211> LENGTH: 11
<212> TYPE: PRT
<213> ORGANISM: Pseudomonas aeruginosa

<400> SEQUENCE: 4

Pro Val Leu Pro Pro Asp Leu Arg Pro Leu Val
1               5                   10

<210> SEQ ID NO 5
<211> LENGTH: 11
<212> TYPE: PRT
<213> ORGANISM: Treponema pallidum

<400> SEQUENCE: 5

Pro Val Ile Pro Pro Asp Leu Arg Pro Met Val
1               5                   10

<210> SEQ ID NO 6
<211> LENGTH: 11
<212> TYPE: PRT
<213> ORGANISM: Borrelia burgdorferi

<400> SEQUENCE: 6

Pro Val Ile Pro Pro Glu Leu Arg Pro Met Val
1               5                   10

<210> SEQ ID NO 7
<211> LENGTH: 11
<212> TYPE: PRT
<213> ORGANISM: Xylella fastidiosa

<400> SEQUENCE: 7

Pro Val Leu Pro Pro Asp Leu Arg Pro Leu Val
1               5                   10

<210> SEQ ID NO 8
<211> LENGTH: 11
<212> TYPE: PRT
<213> ORGANISM: Campylobacter coli
```

-continued

<400> SEQUENCE: 8

Pro Val Leu Pro Pro Asp Leu Arg Pro Leu Val
1               5                   10

<210> SEQ ID NO 9
<211> LENGTH: 11
<212> TYPE: PRT
<213> ORGANISM: Neisseria meningitidis

<400> SEQUENCE: 9

Pro Val Leu Pro Pro Asp Leu Arg Pro Leu Val
1               5                   10

<210> SEQ ID NO 10
<211> LENGTH: 11
<212> TYPE: PRT
<213> ORGANISM: Rickettsia prowazekii

<400> SEQUENCE: 10

Pro Val Ile Pro Pro Glu Ile Arg Pro Leu Val
1               5                   10

<210> SEQ ID NO 11
<211> LENGTH: 11
<212> TYPE: PRT
<213> ORGANISM: Chlamydia trachomatis

<400> SEQUENCE: 11

Pro Val Val Pro Pro Asp Leu Arg Pro Leu Val
1               5                   10

<210> SEQ ID NO 12
<211> LENGTH: 11
<212> TYPE: PRT
<213> ORGANISM: Mycoplasma pneumoniae

<400> SEQUENCE: 12

Pro Val Ile Pro Pro Asp Ile Arg Pro Ile Ile
1               5                   10

<210> SEQ ID NO 13
<211> LENGTH: 11
<212> TYPE: PRT
<213> ORGANISM: Bacillus subtilis

<400> SEQUENCE: 13

Pro Val Ile Pro Pro Glu Leu Arg Pro Met Val
1               5                   10

<210> SEQ ID NO 14
<211> LENGTH: 11
<212> TYPE: PRT
<213> ORGANISM: Staphylococcus aureus

<400> SEQUENCE: 14

Pro Ile Ile Pro Pro Glu Ile Arg Pro Met Ala
1               5                   10

<210> SEQ ID NO 15
<211> LENGTH: 11
<212> TYPE: PRT
<213> ORGANISM: Mycobacterium tuberculosis

<400> SEQUENCE: 15

```
Pro Val Ile Pro Pro Glu Leu Arg Pro Met Val
1               5                   10

<210> SEQ ID NO 16
<211> LENGTH: 11
<212> TYPE: PRT
<213> ORGANISM: Synechocystis sp.

<400> SEQUENCE: 16

Pro Val Ile Pro Pro Asp Leu Arg Pro Met Val
1               5                   10

<210> SEQ ID NO 17
<211> LENGTH: 11
<212> TYPE: PRT
<213> ORGANISM: Mycobacterium tuberculosis

<400> SEQUENCE: 17

Pro Val Leu Pro Pro Glu Leu Arg Pro Leu Val
1               5                   10

<210> SEQ ID NO 18
<211> LENGTH: 11
<212> TYPE: PRT
<213> ORGANISM: Deinococcus radiodurans

<400> SEQUENCE: 18

Pro Val Met Pro Pro Asp Leu Arg Pro Met Val
1               5                   10

<210> SEQ ID NO 19
<211> LENGTH: 11
<212> TYPE: PRT
<213> ORGANISM: Thermus thermophilus

<400> SEQUENCE: 19

Pro Val Leu Pro Pro Asp Leu Arg Pro Met Val
1               5                   10

<210> SEQ ID NO 20
<211> LENGTH: 11
<212> TYPE: PRT
<213> ORGANISM: Thermus aquaticus

<400> SEQUENCE: 20

Pro Val Leu Pro Pro Asp Leu Arg Pro Met Val
1               5                   10

<210> SEQ ID NO 21
<211> LENGTH: 11
<212> TYPE: PRT
<213> ORGANISM: Homo sapiens

<400> SEQUENCE: 21

Val Val Pro Pro Ser Arg Ser Arg Pro Val Ser
1               5                   10

<210> SEQ ID NO 22
<211> LENGTH: 11
<212> TYPE: PRT
<213> ORGANISM: Homo sapiens

<400> SEQUENCE: 22

Pro Val Pro Pro Leu Ser Val Arg Pro Ala Val
1               5                   10
```

```
<210> SEQ ID NO 23
<211> LENGTH: 11
<212> TYPE: PRT
<213> ORGANISM: Homo sapiens

<400> SEQUENCE: 23

Leu Val Pro Pro Leu Cys Phe Arg Pro Ser Val
1               5                   10

<210> SEQ ID NO 24
<211> LENGTH: 10
<212> TYPE: PRT
<213> ORGANISM: Escherichia coli

<400> SEQUENCE: 24

Gly Ser Tyr Ser Leu Val Thr Gln Gln Pro
1               5                   10

<210> SEQ ID NO 25
<211> LENGTH: 6
<212> TYPE: PRT
<213> ORGANISM: Escherichia coli

<400> SEQUENCE: 25

Pro Glu Ser Phe Asn Val
1               5

<210> SEQ ID NO 26
<211> LENGTH: 10
<212> TYPE: PRT
<213> ORGANISM: Haemophilus influenzae

<400> SEQUENCE: 26

Gly Ser Tyr Ser Leu Val Thr Gln Gln Pro
1               5                   10

<210> SEQ ID NO 27
<211> LENGTH: 6
<212> TYPE: PRT
<213> ORGANISM: Haemophilus influenzae

<400> SEQUENCE: 27

Pro Glu Ser Phe Asn Val
1               5

<210> SEQ ID NO 28
<211> LENGTH: 10
<212> TYPE: PRT
<213> ORGANISM: Vibrio cholerae

<400> SEQUENCE: 28

Gly Ser Tyr Ser Leu Val Thr Gln Gln Pro
1               5                   10

<210> SEQ ID NO 29
<211> LENGTH: 6
<212> TYPE: PRT
<213> ORGANISM: Vibrio cholerae

<400> SEQUENCE: 29

Pro Glu Ser Phe Asn Val
1               5

<210> SEQ ID NO 30
<211> LENGTH: 10
```

```
<212> TYPE: PRT
<213> ORGANISM: Pseudomonas aeruginosa

<400> SEQUENCE: 30

Gly Ser Tyr Ser Leu Val Thr Gln Gln Pro
1               5                   10

<210> SEQ ID NO 31
<211> LENGTH: 6
<212> TYPE: PRT
<213> ORGANISM: Pseudomonas aeruginosa

<400> SEQUENCE: 31

Pro Glu Ser Phe Asn Val
1               5

<210> SEQ ID NO 32
<211> LENGTH: 10
<212> TYPE: PRT
<213> ORGANISM: Treponema pallidum

<400> SEQUENCE: 32

Gly Pro Tyr Ser Leu Val Thr Gln Gln Pro
1               5                   10

<210> SEQ ID NO 33
<211> LENGTH: 6
<212> TYPE: PRT
<213> ORGANISM: Treponema pallidum

<400> SEQUENCE: 33

Pro Glu Ser Phe Asn Val
1               5

<210> SEQ ID NO 34
<211> LENGTH: 10
<212> TYPE: PRT
<213> ORGANISM: Borrelia burgdorferi

<400> SEQUENCE: 34

Gly Pro Tyr Ser Leu Val Thr Gln Gln Pro
1               5                   10

<210> SEQ ID NO 35
<211> LENGTH: 6
<212> TYPE: PRT
<213> ORGANISM: Borrelia burgdorferi

<400> SEQUENCE: 35

Pro Glu Ser Phe Asn Val
1               5

<210> SEQ ID NO 36
<211> LENGTH: 10
<212> TYPE: PRT
<213> ORGANISM: Xylella fastidiosa

<400> SEQUENCE: 36

Gly Pro Tyr Ser Leu Val Thr Gln Gln Pro
1               5                   10

<210> SEQ ID NO 37
<211> LENGTH: 6
<212> TYPE: PRT
<213> ORGANISM: Xylella fastidiosa
```

```
<400> SEQUENCE: 37

Pro Glu Ser Phe Asn Val
1               5

<210> SEQ ID NO 38
<211> LENGTH: 10
<212> TYPE: PRT
<213> ORGANISM: Campylobacter jejuni

<400> SEQUENCE: 38

Gly Pro Tyr Ser Leu Val Thr Gln Gln Pro
1               5                   10

<210> SEQ ID NO 39
<211> LENGTH: 6
<212> TYPE: PRT
<213> ORGANISM: Campylobacter jejuni

<400> SEQUENCE: 39

Pro Glu Thr Phe Asn Val
1               5

<210> SEQ ID NO 40
<211> LENGTH: 10
<212> TYPE: PRT
<213> ORGANISM: Neisseria meningitidis

<400> SEQUENCE: 40

Gly Pro Tyr Ser Leu Val Thr Gln Gln Pro
1               5                   10

<210> SEQ ID NO 41
<211> LENGTH: 6
<212> TYPE: PRT
<213> ORGANISM: Neisseria meningitidis

<400> SEQUENCE: 41

Pro Glu Ser Phe Asn Val
1               5

<210> SEQ ID NO 42
<211> LENGTH: 10
<212> TYPE: PRT
<213> ORGANISM: Rickettsia prowazekii

<400> SEQUENCE: 42

Gly Pro Tyr Ser Leu Val Thr Gln Gln Pro
1               5                   10

<210> SEQ ID NO 43
<211> LENGTH: 6
<212> TYPE: PRT
<213> ORGANISM: Rickettsia prowazekii

<400> SEQUENCE: 43

Pro Glu Ser Phe Asn Val
1               5

<210> SEQ ID NO 44
<211> LENGTH: 10
<212> TYPE: PRT
<213> ORGANISM: Chlamydia trachomatis

<400> SEQUENCE: 44

Gly Pro Tyr Ser Leu Val Thr Gln Gln Pro
```

<210> SEQ ID NO 45
<211> LENGTH: 6
<212> TYPE: PRT
<213> ORGANISM: Chlamydia trachomatis

<400> SEQUENCE: 45

Pro Glu Ser Phe Asn Val
1               5

<210> SEQ ID NO 46
<211> LENGTH: 10
<212> TYPE: PRT
<213> ORGANISM: Mycoplasma pneumoniae

<400> SEQUENCE: 46

Gly Pro Tyr Ser Lys Ile Thr Gln Gln Pro
1               5                   10

<210> SEQ ID NO 47
<211> LENGTH: 6
<212> TYPE: PRT
<213> ORGANISM: Mycoplasma pneumoniae

<400> SEQUENCE: 47

Pro Glu Ser Phe Lys Leu
1               5

<210> SEQ ID NO 48
<211> LENGTH: 10
<212> TYPE: PRT
<213> ORGANISM: Bacillus subtilis

<400> SEQUENCE: 48

Gly Pro Tyr Ser Leu Val Thr Gln Gln Pro
1               5                   10

<210> SEQ ID NO 49
<211> LENGTH: 6
<212> TYPE: PRT
<213> ORGANISM: Bacillus subtilis

<400> SEQUENCE: 49

Pro Glu Ser Phe Lys Val
1               5

<210> SEQ ID NO 50
<211> LENGTH: 10
<212> TYPE: PRT
<213> ORGANISM: Staphylococcus aureus

<400> SEQUENCE: 50

Gly Pro Tyr Ser Leu Val Thr Gln Gln Pro
1               5                   10

<210> SEQ ID NO 51
<211> LENGTH: 6
<212> TYPE: PRT
<213> ORGANISM: Staphylococcus aureus

<400> SEQUENCE: 51

Pro Glu Ser Phe Arg Val
1               5

```
<210> SEQ ID NO 52
<211> LENGTH: 10
<212> TYPE: PRT
<213> ORGANISM: Mycobacterium tuberculosis

<400> SEQUENCE: 52

Gly Pro Tyr Ser Met Ile Thr Gln Gln Pro
1               5                   10

<210> SEQ ID NO 53
<211> LENGTH: 6
<212> TYPE: PRT
<213> ORGANISM: Mycobacterium tuberculosis

<400> SEQUENCE: 53

Pro Glu Ser Phe Lys Val
1               5

<210> SEQ ID NO 54
<211> LENGTH: 10
<212> TYPE: PRT
<213> ORGANISM: Synechocystis sp.

<400> SEQUENCE: 54

Gly Pro Tyr Ser Leu Val Thr Gln Gln Pro
1               5                   10

<210> SEQ ID NO 55
<211> LENGTH: 6
<212> TYPE: PRT
<213> ORGANISM: Synechocystis sp.

<400> SEQUENCE: 55

Pro Glu Ser Phe Lys Val
1               5

<210> SEQ ID NO 56
<211> LENGTH: 10
<212> TYPE: PRT
<213> ORGANISM: Aquifex aeolicus

<400> SEQUENCE: 56

Gly Pro Thr Ser Leu Val Thr Gln Gln Pro
1               5                   10

<210> SEQ ID NO 57
<211> LENGTH: 6
<212> TYPE: PRT
<213> ORGANISM: Aquifex aeolicus

<400> SEQUENCE: 57

Pro Glu Ser Phe Lys Val
1               5

<210> SEQ ID NO 58
<211> LENGTH: 10
<212> TYPE: PRT
<213> ORGANISM: Deinococcus radiodurans

<400> SEQUENCE: 58

Gly Pro Thr Ser Leu Ile Thr Gln Gln Pro
1               5                   10

<210> SEQ ID NO 59
<211> LENGTH: 6
<212> TYPE: PRT
```

<213> ORGANISM: Deinococcus radiodurans

<400> SEQUENCE: 59

Pro Glu Ser Phe Lys Val
1               5

<210> SEQ ID NO 60
<211> LENGTH: 10
<212> TYPE: PRT
<213> ORGANISM: Thermus thermophilus

<400> SEQUENCE: 60

Gly Pro Tyr Ser Leu Ile Thr Gln Gln Pro
1               5                   10

<210> SEQ ID NO 61
<211> LENGTH: 6
<212> TYPE: PRT
<213> ORGANISM: Thermus thermophilus

<400> SEQUENCE: 61

Pro Glu Ser Phe Arg Val
1               5

<210> SEQ ID NO 62
<211> LENGTH: 10
<212> TYPE: PRT
<213> ORGANISM: Thermus aquaticus

<400> SEQUENCE: 62

Gly Pro Thr Ser Leu Ile Thr Gln Gln Pro
1               5                   10

<210> SEQ ID NO 63
<211> LENGTH: 6
<212> TYPE: PRT
<213> ORGANISM: Thermus aquaticus

<400> SEQUENCE: 63

Pro Glu Ser Phe Arg Val
1               5

<210> SEQ ID NO 64
<211> LENGTH: 10
<212> TYPE: PRT
<213> ORGANISM: Homo sapiens

<400> SEQUENCE: 64

Gly Ala Arg Asp Arg Val Thr Asn Gln Pro
1               5                   10

<210> SEQ ID NO 65
<211> LENGTH: 6
<212> TYPE: PRT
<213> ORGANISM: Homo sapiens

<400> SEQUENCE: 65

Pro Tyr Val Phe Arg Tyr
1               5

<210> SEQ ID NO 66
<211> LENGTH: 10
<212> TYPE: PRT
<213> ORGANISM: Homo sapiens

<400> SEQUENCE: 66

-continued

```
Gly Pro Ile Gln Ile Leu Asn Arg Gln Pro
1               5                   10

<210> SEQ ID NO 67
<211> LENGTH: 6
<212> TYPE: PRT
<213> ORGANISM: Homo sapiens

<400> SEQUENCE: 67

Pro Tyr Ala Cys Lys Leu
1               5

<210> SEQ ID NO 68
<211> LENGTH: 10
<212> TYPE: PRT
<213> ORGANISM: Homo sapiens

<400> SEQUENCE: 68

Gly Pro Arg Ala Val Leu Thr Arg Gln Pro
1               5                   10

<210> SEQ ID NO 69
<211> LENGTH: 6
<212> TYPE: PRT
<213> ORGANISM: Homo sapiens

<400> SEQUENCE: 69

Pro Tyr Ala Cys Lys Leu
1               5
```

RNA-EXIT-CHANNEL: TARGET AND METHOD FOR INHIBITION OF BACTERIAL RNA POLYMERASE

CROSS-REFERENCE TO RELATED APPLICATIONS

This application is a divisional of U.S. application Ser. No. 10/527,559 filed on Aug. 15, 2005, which is a national phase application under 35 U.S.C. §371 of International Application No. PCT/US2004/016826, filed May 28, 2004 which claims priority to U.S. Provisional Application No. 60/473,485 filed May 28, 2003, the disclosures of which are all hereby incorporated by reference herein.

GOVERNMENT SUPPORT

This invention was supported with U.S. Government funds (NIH RO1-GM41376). Therefore, the Government may have rights in the invention.

BACKGROUND ART

Bacterial infections remain among the most common and deadly causes of human disease. Infectious diseases are the third leading cause of death in the United States and the leading cause of death worldwide (Binder et al., Science 284:1311-1313 (1999)). Multi-drug-resistant bacteria now cause infections that pose a grave and growing threat to public health. It has been shown that bacterial pathogens can acquire resistance to first-line and even second-line antibiotics. (See, Stuart B. Levy, The Challenge of Antibiotic Resistance, in Scientific American, 46-53 (March, 1998); Walsh, C. (2000) Nature 406, 775-781; Schluger, N. (2000) Int. J. Tuberculosis Lung Disease 4, S71-S75; Raviglione et al., (2001) Ann. NY Acad. Sci. 953, 88-97). New approaches to drug development are necessary to combat the ever-increasing number of antibiotic-resistant pathogens.

The present invention provides one such approach, which involves the transcription machinery of bacteria. RNA is synthesized in cellular organisms by a complex molecular machine, known as RNA polymerase ("RNAP"). In its simplest bacterial form, RNAP comprises at least four subunits with a total molecular mass of around 400 kDa. RNAP mediates the transcription of DNA to produce RNA. Bacterial RNAP is a multimeric protein consisting of subunits $\alpha_2$, $\beta$, $\beta'$, and $\omega$. An $\sigma$ factor is required for initiation of transcription by forming a holoenzyme complex.

Transcription involves the following steps (Record et al. 1996): (i) RNAP binds to promoter DNA, to yield an RNAP-promoter closed complex; (ii) RNAP melts ~14 bp of promoter DNA surrounding the transcription start site, to yield an RNAP-promoter open complex; (iii) RNAP begins synthesis of RNA, typically carrying out multiple rounds of abortive initiation (synthesis and release of RNA products <9-11 nt in length), as an RNAP-promoter initial transcribing complex; and (iv), upon synthesis of an RNA product of a critical threshold length of 9-11 nt, RNAP breaks its interactions with promoter DNA and begins to translocate along DNA, processively synthesizing RNA as an RNAP-DNA elongation complex.

Currently, there are a few known antibiotics that target RNAP, most notably, rifampicin and rifampicin analogs (See Mitchison, D. (2000) Int. J. Tuberculosis Lung Disease 4, 796-806). Rifampicin is the only anti-tuberculosis compound able to rapidly clear infection and prevent relapse. Without rifampicin, treatment lengths must increase from 6 months to at least 18 months to ensure prevention of relapse. Rifampicin acts by specifically inhibiting RNAP (Campbell et al., (2001) Cell 104, 901-912). Rifampicin binds to a site adjacent to the active center of bacterial RNAP, the exit channel, and physically prevents synthesis of products longer than ~4 nucleotides. Unfortunately, tuberculosis strains resistant to rifampicin (and rifampicin analogs) are becoming widespread, effectively removing rifampicin from the therapeutic arsenal. There is a need for novel antibiotics that target the same bacterial enzyme as rifampicin, namely RNAP (and thus that have the same biochemical and therapeutic effects as rifampicin). There is also a need to develop methods for identifying antibiotics that interfere with bacterial RNAP.

Recently crystallographic structures have been determined for bacterial RNAP and eukaryotic RNAP II, and, based on the crystallographic structures, biophysical results, and biochemical results, structural models have been proposed for transcription initiation and elongation complexes (Zhang et al., (1999) Cell 98, 811-824; Cramer et al., (2000), Science 288, 640-649; Naryshkin et al., (2000) Cell 101, 601-611; Kim et al., (2000) Science 288, 1418-1421; Korzheva et al., (2000) Science 289, 619-625; Ebright, R. (2000) J. Mol. Biol. 304, 687-689; Cramer et al., (2001) Science 292, 1863-1876; Gnatt et al., (2001) Science 292, 1876-1882; Mekler et al., (2002) Cell 108, 599-614; Murakami et al., (2002) Science 296, 1280-1284; Murakami et al., (2002) Science 296, 1285-1290; Vassylyev et al., (2002) Nature 417, 712-719; Bushnell et al., (2004) Science 303, 983-988; Westover et al., (2004) Science 303, 1014-1016). The structural models include an approximately 30 Å long, 15 Å wide channel, known as the "RNA-exit-channel," that connects the RNAP active-center cleft to the RNAP exterior. In transcription initiation complexes, transcription initiation factors occupy this channel: i.e., initiation factor $\sigma$ region 3.2 (also known as the "$\sigma$R3/$\sigma$R4 linker" or "$\sigma$3/$\sigma$4 linker") in the case of bacterial transcription initiation complexes and transcription initiation factor IIB N-terminal domain in the case of eukaryotic RNAP II transcription initiation complexes. In transcription elongation complexes, the nascent RNA product occupies this channel.

SUMMARY OF THE INVENTION

Applicant has discovered that a region within the RNAP RNA-exit-channel comprising two short peptide segments of the RNAP $\beta$ subunit and one short peptide segment of the RNAP $\beta'$ subunit is conserved in amino-acid sequence in bacterial species, including both Gram-positive bacteria and Gram-negative bacteria. Throughout the following specification, this region is referred to as the "target," and the three short peptide segments collectively are referred to as the "homologous RNA-exit-channel amino-acid sequence." Applicant further has discovered that this region is not conserved, and in fact is radically different, in amino-acid sequence in eukaryotic RNAP, such as human RNAP I, human RNAP II, and human RNAP III. Applicant further has discovered that this region form an approximately 10 Å wide shallow pocket within the wall of the RNAP RNA exit channel.

Accordingly, a first aspect of the present invention is directed to a method for identifying agents that bind to a bacterial RNAP homologous RNA-exit-channel amino-acid sequence, comprising preparing a reaction solution comprising the agent to be tested and an entity containing a homologous RNA-exit-channel amino-acid sequence; and detecting presence or amount of binding. In a preferred embodiment, detection or quantitation of binding is conducted relative to binding of the agent to an entity containing an altered homologous RNA-exit-channel amino-acid sequence.

Another aspect of the present invention is directed to a method for identifying agents that inhibit an activity of bacterial RNAP via binding to a homologous RNA-exit-channel amino-acid sequence. This aspect entails preparing a reaction solution comprising the agent to be tested, a catalytic entity containing a homologous RNA-exit-channel amino-acid sequence, and a substrate for the entity; and determining extent of inhibition of RNAP activity via binding of the agent to the homologous RNA-exit-channel amino-acid sequence.

In some preferred embodiments, binding or inhibition is compared to binding or inhibition by lipiarmycin (Lpm). Lpm is a macrocyclic antibiotic effective against both Gram-positive bacteria and Gram-negative bacteria (Coronelli et al., (1975) *J. Antibiot.* 28, 253-259). Lpm functions by inhibiting bacterial RNAP (Sergio et al., (1975) *J. Antibiot.* 1975, 543-549; Talpaert et al., (1975) *Biochem. Biophys. Res. Commun.* 63, 328-334; Sonenshein et al., (1977) *J. Bacteriol.* 132, 73-79; Sonenshein et al., (1979) *J. Mol. Biol.* 127, 55-72). The present invention provides that Lpm inhibits bacterial RNAP by binding to a determinant that includes residues within the bacterial RNAP homologous RNA-exit-channel amino-acid sequence. The present invention also provides for the identification of potential antibacterial agents or antibiotics that, because they interact with residues that are conserved in bacterial RNAP, have broad-spectrum antibacterial activity. It also provides for the identification of potential anti-bacterial agents or antibiotics that, because they interact with residues that are not conserved in eukaryotic RNAP, are relatively non-disruptive to normal cellular functions of eukaryotes.

It is anticipated that compounds identified according to the target and method of this invention would have applications not only in antibacterial therapy, but also in: (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNAP (biotechnology applications), (e) regulation of bacterial gene expression (biotechnology applications), and (f) antisepsis (antiseptics, disinfectants, and advanced-materials applications).

These and other aspects of the present invention will be better appreciated by reference to the following drawings and detailed description.

The file of this patent contains at least one drawing executed in color. Copies of this patent with color drawing(s) will be provided by the Patent and Trademark Office upon request and payment of the necessary fee.

BRIEF DESCRIPTION OF THE DRAWINGS

FIG. 1A illustrates sequence alignments for the bacterial RNAP homologous RNA-exit-channel amino-acid sequences within rpoB (β) from *Escherichia coli*; and corresponding residues of *Haemophilus influenzae*, *Vibrio cholerae*, *Pseudomonas aeruginosa*, *Treponema pallidum*, *Borrelia burgdorferi*, *Xyella fastidiosa*, *Camploacter jejuni*, *Neisseria meningitides*, *Rickettsia prowazekii*, *Chlamydia trachomatis*, *Mycoplasma pneumoniae*, *Bacillus subtilis*, *Staphylococcus aureus*, *Mycobacterium tuberculosis*, *Synechocystis* sp., *Aquifer aeolicus*, *Deinococcus radiodurans*, *Thermus thermophilus*, and *Thermus aquaticus*; and corresponding residues of the largest subunits of human RNAP I, human RNAP II, and human RNAP III.

FIG. 1B illustrates sequence alignments for the bacterial RNAP homologous RNA-exit-channel amino-acid sequences within rpoC (β') from *Escherichia coli*; and corresponding residues of *Haemophilus influenzae*, *Vibrio cholerae*, *Pseudomonas aeruginosa*, *Treponema pallidum*, *Borrelia burgdorferi*, *fastidiosa*, *Camploacter jejuni*, *Neisseria meningitides*, *Rickettsia prowazekii*, *Chlamydia trachomatis*, *Mycoplasma pneumoniae*, *Bacillus subtilis*, *Staphylococcus aureus*, *Mycobacterium tuberculosis*, *Synechocystis* sp., *Aquifer aeolicus*, *Deinococcus radiodurans*, *Thermus thermophilus*, and *Thermus aquaticus*; and corresponding residues of the largest subunits of human RNAP I, human RNAP II, and human RNAP III.

BEST MODE OF CARRYING OUT THE INVENTION

Figure 2:
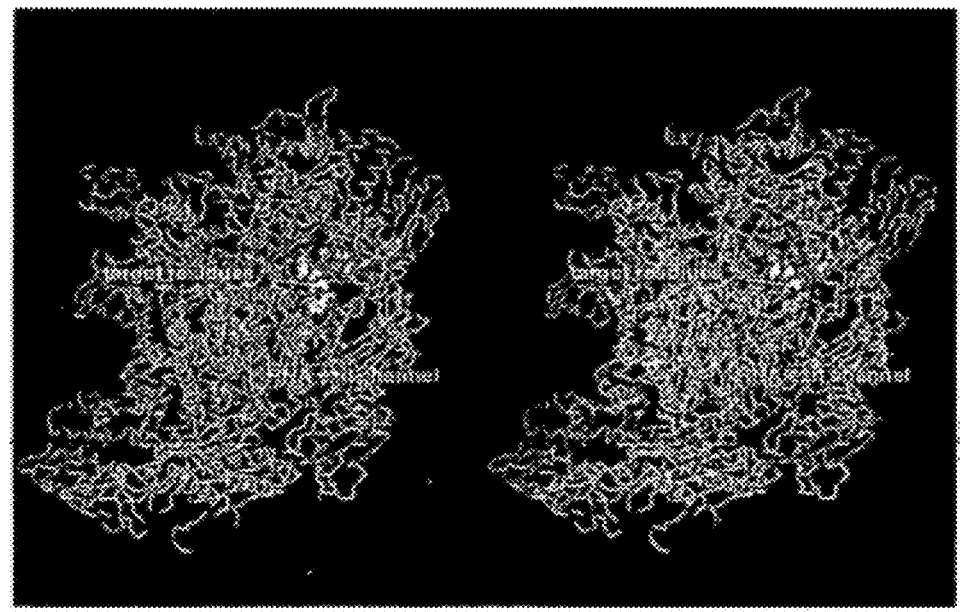
FIG. 2 illustrates a model of the three-dimensional structure of *Thermus thermophilius* RNAP showing the location of bacterial RNAP homologous RNA-exit-channel amino-acid sequence. The view is directly into the RNA-exit-channel of RNAP—toward the active-center cleft. Atomic coordinates are based on the crystallographic structure of *Thermus thermophilius* RNAP at 2.6 Å resolution (Vassyleyev et al., 2002; PDB accession 1IW7; σ subunit omitted for clarity).

The present invention provides methods of designing specific inhibitors of bacterial RNAP, the enzyme responsible for transcription. The invention provides targets and methods for specific binding and inhibition of RNAP from bacterial species. The invention has applications in control of bacterial gene expression, control of bacterial growth, antibacterial chemistry, and antibacterial therapy.

Recently, crystallographic structures have been determined for bacterial RNAP and eukaryotic RNAP II (Zhang et al., (1999) *Cell* 98, 811-824; Cramer et al., (2000) *Science* 288, 640-649; Cramer et al., (2001) *Science* 292, 1863-1876; Ebright, R. (2000) *J. Mol. Biol.* 304, 687-689; Gnatt et al., (2001) *Science* 292, 1876-1882; Murakami et al., (2002) *Science* 296, 1280-1284; Murakami et al., (2002) *Science* 296, 1285-1290; Vassylyev et al., (2002) *Nature* 417, 712-719; Bushnell et al., (2004) *Science* 303, 983-988; Westover et al., (2004) *Science* 303, 1014-1016). Based on these crystallographic structures, and biophysical and biochemical results, structural models have been proposed for transcription initiation and elongation complexes ((Naryshkin et al., (2000) *Cell* 101, 601-611; Kim et al., (2000) *Science* 288, 1418-1421; Korzheva et al., (2000) *Science* 289, 619-625; Ebright, R. (2000) *J. Mol. Biol.* 304, 687-689; Gnatt et al., (2001) *Science* 292, 1876-1882; Mekler et al., (2002) *Cell* 108:599-614; Murakami et al., (2002) *Science* 296, 1280-1284; Murakami et al., (2002) *Science* 296, 1285-1290; Vassylyev et al., (2002) *Nature* 417, 712-719; Bushnell et al., (2004) *Science* 303, 983-988; Westover et al., (2004) *Science* 303, 1014-1016).).

The structural models include an approximately 30 Å long, 15 Å wide channel, known as the "RNA-exit-channel," that connects the RNAP active-center cleft to the RNAP exterior. In transcription initiation complexes, transcription initiation factors occupy this channel: i.e., initiation factor σ region 3.2 (also known as the "σR3/σR4 linker" or "σ3/σ4 linker") in the case of bacterial transcription initiation complexes and transcription initiation factor IIB N-terminal domain in the case of eukaryotic RNAP II transcription initiation complexes. In transcription elongation complexes, the nascent RNA product occupies this channel.

The structural models imply that the RNAP RNA-exit-channel plays roles in biochemical activities important for function of RNAP in transcription initiation and elongation, including: interaction between RNAP and initiation factors, interaction between RNAP and DNA (which is modulated by initiation factors), interaction between RNAP and initiating NTPs (which is modulated by initiation factors), and interaction between RNAP and the nascent RNA product.

It has now been found, and is disclosed herein, that binding of a small molecule within the RNAP RNA-exit-channel inhibits at least two of these biochemical activities. Specifically, it has now been found, and is disclosed herein, that binding of a small molecule within the RNAP RNA-exit-channel disrupts RNAP-initiation-factor interactions and disrupts RNAP-DNA interactions.

The present invention includes the discovery that a region within the bacterial RNAP RNA-exit-channel comprising residues corresponding to, and alignable with, 1251, 1256, and 1321 of the β subunit of RNAP from *Escherichia coli* and residues 248-249 of the β' subunit of RNAP from *Escherichia coli* (the "homologous RNA-exit-channel amino-acid sequence" or "target"; FIG. 1) is a useful target for compounds that block transcription. The corresponding residues in RNAP from *Bacillus subtilis* RNAP are residues 1056, 1061, and 1126 of the β subunit and residues 237-238 of the β' subunit of RNAP (FIG. 1). It was found that these residues are invariant or nearly invariant in RNAP from bacterial species, but are radically different in RNAP from eukaryotic species (FIG. 1). It further was found that these residues form an approximately 10 Å wide shallow pocket within the wall of the RNAP RNA-exit-channel (FIG. 2).

The target is located within the bacterial RNAP RNA-exit-channel, a ~30 Å long, ~15 Å wide tunnel that mediates multiple biochemical activities of bacterial RNAP, including: interaction with σ region 3.2 in free RNAP holoenzyme, interaction with σ region 3.2 in transcription initiation complexes, interaction with the nascent RNA product in transcription elongation complexes, and extrusion of the nascent RNA product in transcription elongation complexes. The location of the target within the bacterial RNAP RNA-exit-channel is such that binding to the target of a sufficiently large molecule would be predicted to block the RNA-exit-channel and thereby to inhibit some or all of the above-listed biochemical activities. The location of the target within the RNAP RNA-exit-channel also is such that binding to the target of a sufficiently large molecule would be predicted to interfere with interactions between RNAP and DNA (both indirectly, through disruption of RNAP-σ-region-3.2 interactions, and directly through steric clash with the DNA template strand).

The target referred to above in *Escherichia coli* RNAP is similar in amino-acid sequence to that of most or all other species of bacterial RNAP, and is referred to herein as the "homologous bacterial RNAP RNA-exit-channel amino-acid sequence". (For example, amino acid residues 1251, 1256 and 1321 of the β subunit and residues 248-249 and 337 of the β' subunit of RNAP from *Escherichia coli* exhibit high similarity to residues 1056, 1061, and 1126 of the β subunit and residues 237-238 and 326 of the β' subunit of *Bacillus subtilis* RNAP (FIG. 1).) Thus, the discovery of a molecule that binds to the target and inhibits an activity associated with the RNA-exit-channel in *Escherichia coli* RNAP also is likely to bind to the target an inhibit an activity associated with the RNA-exit-channel in other species of bacterial RNAP. Therefore, molecules found to have antibiotic activity (through binding to the target and inhibiting an activity associated with the RNA-exit-channel) against *Escherichia coli* are likely to be found to have antibiotic activity against other bacterial species.

In contrast, the target differs radically in amino acid sequence between bacterial RNAP and eukaryotic RNAP, including human RNAP I, human RNAP II, and human RNAP III. This allows for the identification of molecules that bind, in a target-dependent fashion, to bacterial RNAP, but that do not bind, or that bind substantially less well, to eukaryotic RNAP. This also allows for the identification of molecules that inhibit, in a target-dependent fashion, an activity of to bacterial RNAP, but that do not inhibit, or that inhibit substantially less well, an activity of eukaryotic RNAP. This differentiation is important, because it permits the identification of bacterial-RNAP-selective binding molecules and bacteria-selective inhibitors.

The invention provides, by way of example only, a target region corresponding to, and alignable with, residues 1251, 1256, and 1321 of the β subunit and residues 248-249 of the β' subunit of RNAP from *Escherichia coli*; as well as corresponding residues of the β' subunit of RNAP from *Bacillus subtilis, Haemophilus influenzae, Vibrio cholerae, Pseudomonas aeruginosa, Treponema pallidum, Borrelia burgdorferi, Ayella fastidiosa, Campylobacter jejuni, Neisseria meningitidis, Rickettsia prowazekii, Thermotoga maritima, Chlamydia trachomatis, Mycoplasma pneumoniae, Staphylococcus aureus, Mycobacterium tuberculosis, Synechocystis* sp., *Aquifex aeolicus, Deinococcus radiodurans, Thermus thermophilus*, and *Therms aquaticus*. This target is the bacterial RNAP homologous RNA-exit-channel amino-acid sequence.

The invention also provides a molecule that binds to RNAP from a bacterial species, making specific interactions with at least one residue within the set of residues corresponding to, and alignable with, residues 1251, 1256, and 1321 of the β subunit and residues 248-249 of the β' subunit of RNAP from *Escherichia coli*.

The invention also provides a compound that inhibits enzymatic activity of RNAP from a bacterial species making specific interactions with at least one residue within the set of residues corresponding to, and alignable with, residues 1056, 1061, and 1126 of the β subunit of RNAP and residues 237-238 of the 13' subunit of RNAP from *Bacillus subtilis*.

The invention provides identification of a inhibitory compound by screening of a chemical library for molecules that: (a) bind to RNAP from a bacterial species, and (b) do not bind, or bind less well, to a derivative of RNAP from a bacterial species that has at least one amino acid substitution, deletion, or insertion, in an homologous RNA-exit-channel amino-acid sequence.

The invention also provides identification of a inhibitory compound by screening of a chemical library for molecules that: (a) inhibit enzymatic activity of RNAP from a bacterial species, and (b) do not inhibit enzymatic activity, or inhibit enzymatic activity less well, of a derivative of RNAP from a bacterial species that has at least one amino acid substitution, deletion, or insertion, in a bacterial RNAP homologous RNA-exit-channel amino-acid sequence.

The invention also provides identification of an inhibitory compound by screening of a chemical library for molecules that compete with a molecule specific for a bacterial RNAP homologous RNA-exit-channel amino-acid sequence containing a detectable group for binding to RNAP from a bacterial species.

The invention also provides identification of an inhibitory compound by screening of a chemical library for molecules that alter the interaction of a region 3.2 within RNAP from a bacterial species.

The invention also provides identification of a molecule specific for a bacterial RNAP homologous RNA-exit-channel amino-acid sequence by screening a chemical library for molecules that alter the interaction of RNA with RNAP from a bacterial species.

The invention also provides identification of a molecule specific for a bacterial RNAP homologous RNA-exit-channel amino-acid sequence by screening a chemical library for molecules that inhibit open-complex formation by RNAP from a bacterial species.

The invention also provides for use of a molecule specific for a bacterial RNAP homologous RNA-exit-channel amino-acid sequence to identify, isolate, and/or immobilize RNAP from a bacterial species.

The invention also provides for use of a molecule specific for a bacterial RNAP homologous RNA-exit-channel amino-acid sequence to control bacterial gene expression.

The invention also provides for use of a molecule specific for a bacterial RNAP homologous RNA-exit-channel amino-acid sequence to control bacterial growth.

The invention also provides for use of a molecule specific for a bacterial RNAP homologous RNA-exit-channel amino-acid sequence as an antibacterial agent.

One preferred aspect of the invention provides for a molecule specific for a bacterial RNAP homologous RNA-exit-channel amino-acid sequence that binds to RNAP from a bacterial species, but does not bind, or binds less well, to RNAP from a mammalian species.

Another preferred aspect of the invention provides for a molecule specific for a bacterial RNAP homologous RNA-exit-channel amino-acid sequence that inhibits biochemical activity of RNAP from a bacterial species, but does not inhibit biochemical activity, or inhibits biochemical activity less well, of RNAP from a mammalian species.

Another preferred aspect of the invention provides for a molecule specific for a bacterial RNAP homologous RNA-exit-channel amino-acid sequence that binds to and/or inhibits RNAP from a broad spectrum of bacterial species.

Another preferred aspect of the invention provides for a molecule specific for a bacterial RNAP homologous RNA-exit-channel amino-acid sequence that binds to and/or inhibits RNAP from a broad spectrum of both Gram-negative bacterial species.

Another preferred aspect of the invention provides for a molecule specific for a bacterial RNAP homologous RNA-exit-channel amino-acid sequence that binds to and/or inhibits RNAP from a broad spectrum of Gram-positive bacterial species.

Another preferred aspect of the invention provides for a molecule specific for a bacterial RNAP homologous RNA-exit-channel amino-acid sequence that binds to and/or inhibits RNAP from a narrow spectrum of bacterial species.

Another preferred aspect of the invention provides for a molecule that binds to and/or inhibits RNAP from *Escherichia coli*, making specific interactions with at least one residue within the set consisting of residues 1251, 1256, and 1321 of the β subunit and residues 248-249 of the β' subunit of RNAP from *Escherichia coli*.

Another preferred aspect of the invention provides for a molecule that binds to and/or inhibits RNAP from *Bacillus subtilis*, making specific interactions with at least one residue within the set consisting of residues 1056, 1061 and 1126 of the β subunit and residues 237-238 and 326 of the β' subunit of RNAP from *Bacillus subtilis*.

The present invention further relates to a method for identifying molecules that bind to the RNA-exit-channel with an assay for molecules that bind to RNAP in a RNA-exit-channel-specific fashion. In one embodiment, *Escherichia coli* RNAP, or a fragment thereof containing the RNA-exit-channel, is used as the test protein for binding, and a derivative of said RNAP or RNAP fragment having at least one of a substitution, an insertion, or a deletion within the RNA-exit-channel is used as the control protein for target-site specificity of binding. "Hits" may be analyzed for binding and inhibition of Gram-negative-bacterial RNAP, Gram-positive-bacterial RNAP, and eukaryotic RNAP I, RNAP III and RNAP III, in vivo and in vitro. "Hits" may also be characterized structurally by x-ray diffraction analysis of co-crystals with RNAP or an RNAP fragment containing the RNA-exit-channel.

The invention also provides strategies to identify small-molecule inhibitors from compound libraries. By way of example, two strategies are described as follows: (a) selection of molecules that bind to RNAP, or a fragment thereof, in a RNA-exit-channel-dependent fashion (affinity selection of phage-displayed linear and cyclic decapeptide libraries), and (b) screening for molecules that inhibit transcription in a RNA-exit-channel-dependent fashion (iterative deconvolution of solution-phase linear and cyclic D-hexapeptide libraries). In each case, the invention provides the use of a wild-type bacterial RNAP, or fragment thereof, as the test protein for binding/inhibition, and a derivative of bacterial RNAP, or a fragment thereof, having at least one of a substitution, an insertion, or a deletion within the RNA-exit-channel as the control protein for RNA-exit-channel-dependence of binding/inhibition.

The invention also provides for a method of identifying a compound for use as an inhibitor of bacterial RNAP comprising: analyzing a compound or a compound library, that involves docking to, modeling of, geometric calculations with, and/or energetic calculations with, a portion of the structure of an RNAP from a bacterial species comprising at least one residue within the set of residues corresponding to, and alignable with, the target.

The invention provides for at least four drug-discovery assay methods: a) screening based on binding of a compound within the RNA-exit-channel of a bacterial RNAP or fragment thereof; b) screening based on inhibition of an activity associated with the RNA-exit-channel of a bacterial RNAP or fragment thereof; c) screening based on displacement of a derivative of a region 3.2, containing a detectable group, from the RNA-exit-channel of a bacterial RNAP of fragment thereof; and d) screening based on displacement of a compound, containing a detectable group, from the RNA-exit-channel of a bacterial RNAP or a fragment thereof.

One of the embodiments of the present invention is an assay system designed to identify compounds that bind a bacterial RNAP, or a fragment thereof, in a manner that requires the RNA exit channel. The assay is designed to measure the binding of a compound to a determinant that includes at least one amino acid residue contained within a set of amino acid residues identifiable by sequence alignment and/or structure alignment as corresponding to amino-acid residues 1251, 1256, and 1321 of the β subunit and residues 248-249 of the β' subunit of RNAP from *Escherichia coli*.

One of the embodiments of the present invention is an assay system designed to identify compounds that inhibit an activity of a bacterial RNAP, a fragment thereof, in a manner that requires the RNA-exit-channel. The assay is designed to measure the inhibition of an activity, said inhibition involving the binding of a compound to a determinant that includes at least one amino acid residue contained within a set of amino acid residues identifiable by sequence alignment and/or structure alignment as corresponding to amino-acid residues 1251, 1256, and 1321 of the β subunit and residues 248-249 of the β' subunit of RNAP from *Escherichia coli*.

Another embodiment of the present invention is an assay designed to measure the binding of a compound to a bacterial RNAP derivative, or a fragment thereof, containing at least one amino acid substitution, insertion, or deletion within a set of amino acid residues identifiable by sequence alignment and/or structure alignment as corresponding to amino-acid residues 1251, 1256, and 1321 of the β subunit and residues 248-249 of the β' subunit of RNAP from *Escherichia coli*.

Another embodiment of the present invention is an assay designed to measure the inhibition of an activity of a bacterial RNAP derivative, or a fragment thereof, containing at least one amino acid substitution, insertion, or deletion within a set of amino acid residues identifiable by sequence alignment and/or structure alignment as corresponding to amino-acid residues 1251, 1256, and 1321 of the β subunit and residues 248-249 of the β' subunit of RNAP from *Escherichia coli*.

Isolation of RNAP:

The bacterial RNAP, or RNAP derivative, can be isolated from bacteria, produced by recombinant methods, or produced through in vitro protein synthesis. Various compounds can be introduced to determine whether a tested compound binds to, inhibits an activity of, or displaces a detectable-group containing molecule from, the bacterial RNAP or RNAP derivative in a RNA-exit-channel-dependent manner.

Tested compounds can include antibodies, peptides, and various chemical compounds. Additionally, with the known amino acid sequence for a particular RNAP, one of skill in the art could design specific inhibitors.

The assay can be performed in vivo or in vitro and thus does not necessarily require isolation of the RNAP.

The tested compounds can be chosen from chemical libraries, or a computer model can be used to choose compounds that are likely to be effective based on the known structure of the RNA-exit-channel and the structure of the compound.

The compounds can also be tested for competitive inhibition. Preferred strategies for identifying inhibitors include: 1) through affinity selection of phage-displayed linear and cyclic decapeptide libraries, and 2) through iterative deconvolution of solution-phase linear and cyclic D-hexapeptide libraries. One of wild-type *Escherichia coli* RNAP and wild-type *Bacillus subtilis* RNAP is the preferred test protein for binding and inhibition. One of a derivative of *Escherichia coli* RNAP having at least one substitution in the target and a derivative of *Bacillus subtilis* RNAP having at least one substitution in the target is the preferred control protein. Deconvolution essentially entails the resynthesis of that combinatorial pool or mixture that are found to be active in screening against a target of interest. Resynthesis may result in the generation of a set of smaller pools or mixtures, or a set of individual compounds. Rescreening and iterative deconvolution are performed until the individual compounds that are responsible for the activity observed in the screens of the parent mixtures are isolated.

Phage-Display Approach:

Tens of millions of short peptides can be easily surveyed for tight binding to an antibody, receptor or other binding protein using an "epitope library." (See (1990) *Science* 249: 386; (1990) Science 249:404; and (1990) Proc. Natl. Acad. Sci. 87:6378). The library is a vast mixture of filamentous phage clones, each displaying one peptide sequence on the virion surface. The survey is accomplished by using the binding protein to affinity-purify phage that display tight-binding peptides and propagating the purified phage in *Escherichia coli*. The amino acid sequences of the peptides displayed on the phage are then determined by sequencing the corresponding coding region in the viral DNA's. Potential applications of the epitope library include investigation of the specificity of antibodies and discovery of mimetic drug candidates.

"Fusion phage" is filamentous bacteriophage vectors in which foreign antigenic determinants are cloned into phage gene III and displayed as part of the gene III protein (pIII) at one tip of the virion. Fusion phage whose displayed determinant binds an antibody (Ab) can be selected from a vast background of nonbinding phage by affinity purification (AP) as follows: First, phage are reacted with biotinylated Ab (bio-Ab), then diluted and placed on a streptavidin-coated petri dish, thereby specifically attaching Ab-reactive phage to the plastic surface through the Ab-biotin-streptavidin bridge. Free phage is washed away, and bound phage eluted in acid and used to infect *Escherichia coli* cells. A single round of AP can enrich Ab-binding phage by as much as a factor of $10^5$ relative to unreactive phage; further enrichment is achieved by further rounds of AP after amplification on agar medium. Thus, Ab serves as a powerful selective agent favoring the target clones, so that vast numbers of phage can be surveyed.

The idea of using fusion phage to develop an "epitope library" (Parmley and G. P. Smith, (1988) Gene 73:305) was inspired by the synthetic "mimotope" strategy of Geysen et al. (See *Synthetic Peptides as Antigens; Ciba Foundation Symposium* 119, R. Porter and J. Wheelan, Eds. (Wiley, New York. 1986), pp. 131-149). By synthesizing peptide mixtures on plastic pins and assessing their ability to bind an Ab against a protein antigen, these workers delineated a peptide that mimics a discontinuous epitope—an Ab-binding determinant composed of residues distant in the primary sequence but adjacent in the folded structure. They called these peptide mimics mimotopes. In this way, ligands can be discovered for an Ab whose specificity is not known in advance.

Fusion phage displaying short cloned peptides is infectious analogs of chemically synthesized mimotopes, with the key advantages of replicability and clonability. A large library of such phage—an "epitope library"—may display tens of millions of peptide epitopes. The peptides can in effect be individually surveyed for binding to an Ab or other binding protein by affinity purifying reactive phage from the library, propagating individual phage clones, and sequencing the relevant part of their DNA's to determine the amino acid sequences of their displayed peptides. A survey based on the epitope library undoubtedly would be imperfect because of bias introduced by the biology of the phage and other factors; still, it represents a powerful approach to the study of the specificity of Ab's and other binding proteins. (See Scott and Smith (1990) *Science* 249:386; Devlin et al., (1990) *Science* 249:404; Ciwirla et al., (1990) *Proc. Nat'l Acad. Sci.* 87:6378; McLafferty et al., (1993) *Gene* 128:29; Alessandra et al., (1993) *Gene* 128:51; McConnell et al., (1994) *Gene* 151:115, which are incorporated herein by reference).

Iterative-Deconvolution and Positional-Scanning Approaches

See the following reference for a general discussion of iterative deconvolution: (Ostresh et al., (1996) *Meths. Enzym.* 267:220, which is incorporated herein by reference). The practical development of synthetic combinatorial libraries (SCLs) made up of tens of millions of compounds has proven to be a powerful source for the identification of novel biologically active compounds such as analgesics, antibacterials, antifungals, and enzyme inhibitors. (See Pinilla et al., (1994) *Drug Dev. Res.* 33:133; Pinilla et al., (1995) *Pept. Sci.* 37:221; Gallop et al., (1994) *J. Med. Chem.* 37:1233). In particular, a range of new compounds having potent antimicrobial and/or antifungal activities has been rapidly identified from pools of millions of compounds. (See Blondelle et al., (1995) *J. Appl. Bacteriol.* 78:39; Blondelle et al., (1994) *Antimicrob. Agent*

Chemother. 38:2280; Ostresh et al., (1994) Proc. Nat'l. Acad. Sci. U.S.A. 91:11138; Houghten et al., (1992) Bio Techniques 13:412; Houghten et al., (1991) Nature 354:84).

Nonsupport-bound SCLs, originally composed of millions of peptides, are known to be usable in virtually any assay system (including those involving membrane-bound acceptors or whole cell organisms). In an expansion of SCL concepts and diversities, the original peptide SCLs have been transformed (i.e., peralkylated and/or exhaustively reduced) using a "libraries from libraries" approach (Ostresh et al., (1994) Proc. Natl. Acad. Sci. U.S.A. 91:11138; Dörner et al., in "Peptides 1994: Proceedings of the 23rd European Peptide Symposium" (H. L. S. Maia, ed.), p. 463. Escom, Leiden, 1995; and Cuervo et al., Id. at page 465) to yield peptidomimetic and organic libraries having entirely different physical, chemical, and biological properties relative to the peptide SCLs used as starting materials. The screening of such libraries has yielded active compounds derived from entirely different sequences than the active peptides previously identified from the starting SCLs using the same assay.

Two approaches can be employed for the structural deconvolution of active compounds from assay data using nonsupport-bound SCLs: the "iterative" approach and the "positional scanning" approach. In addition, two synthetic methods can be used for the incorporation of multiple functionalities at diverse positions within an SCL. As first illustrated for peptides, (See Houghten et al., (1992) Bio Techniques 13:412; and Houghten et al., (1991) Nature 354: 84, which are incorporated herein by reference). The first synthetic method, known as the "divide, couple, and recombine" (DCR) (Id.) or "split resin" (Lam et al., (1991) Nature 354:82) method, has typically been used with the iterative deconvolution approach. The second synthetic method, which involves the use of a predefined chemical ratio of protected amino acids at each coupling step for incorporation of mixture positions, Ostresh et al., (1994) Biopolymers 34:1681) has been developed for use with the positional scanning deconvolution process (Pinilla et al., (1992) BioTechniques 13:901). This latter method offers the advantage that both defined and mixture positions are easily incorporated at any position in a sequence.

These synthesis and deconvolution methods have been used to identify individual active compounds in a wide variety of SCLs and assays. (Pinilla et al., (1994) Drug Dev. Res. 33:133; Pinilla et al., (1995) Pept. Sci. 37:221). More specifically, individual compounds from nonsupport-bound SCLs have been identified which have potent antimicrobial activity against gram-positive bacteria (Staphylococcus aureus, Streptococcus sanguis), gram-negative bacteria (Escherichia coli, Pseudomonas aeruginosa), and fungi (Candida albicans). The iterative deconvolution approach will be illustrated here for the preparation of a dual-defined position hexapeptide SCL, designated OOXXXX—NH$_2$ (where O represents a defined amino acid, and X represents a mixture of amino acids) using the DCR method. The mixtures making up this library have been assayed for antimicrobial and/or antifungal activity (Blondelle et al., (1995) Trends Anal. Chem. 14:83; Houghten et al., (1992) Bio Techniques 13:412; and Houghten et al., (1991) Nature 354:84) in order to identify the first two amino acid residues of active hexapeptide sequences. The remaining four positions were then identified sequentially through an iterative process of synthesis and screening. This process can be completed in 6 to 10 weeks (four separate iterative synthesis steps are required). The positional scanning approach, involves the screening of separate single position SCLs to identify the most effective amino acids at each position of the sequence. When used in concert, this information can be used to identify individual active sequences. This process can be completed in approximately 2 weeks (only one synthesis step is required for confirmation of activity).

Both iterative and positional scanning peptide SCLs are used as starting materials for the generation of peptidomimetic SCLs using the "libraries from libraries" approach.

Peptide libraries for iterative and positional-scanning approaches are prepared using the DCR process (Houghten et al., (1991) Nature 354:84) in conjunction with simultaneous multiple peptide synthesis (SMPS) (Houghten, (1985) Proc. Natl. Acad. Sci. U.S.A. 82:5131) also known as the "tea bag" approach. Standard t-butyloxycarbonyl (Boc)-based peptide synthesis protocols are typically used to couple protected amino acids (Sachem, Torrance, Calif.) to methylbenzhydrylamine (MBHA)-derivatized polystyrene resin (Peninsula, Belmont, Calif.). Fluorenylmethyloxycarbonyl (Fmoc)-based chemistry strategies can also be used. During preparation of the initial library, a portion of each resin mixture (i.e., X-resin, XX-resin, XXX-resin, etc) is held back for synthesis of the subsequent peptide mixtures during the iterative process in which additional positions are sequentially defined. While up to 76 amino acids have been used in the mixture positions, cysteine is normally omitted from the mixture positions of an SCL to prevent polymerization side reactions. It should be noted that for libraries synthesized by the DCR method, the number of resin beads used should be 10 to 100 times higher than the final number of individual compounds in a resin mixture in order to ensure statistical representation of each peptide in the library (Gallop et al., (1994) J. Med. Chem. 37:1233). The generation of a dual-defined position SCL made up of L-amino acid hexapeptides (designated OOXXXX—NH$_2$) is described here to illustrate the DCR methodology. This library contains approximately 64 million ($20^6$) different peptides.

The practical use of nonsupport-bound combinatorial libraries represents an important breakthrough in all areas of basic research and drug discovery. The use of a wide variety of chemical transformations permits a range of peptidomimetic libraries to be generated, which greatly expands the chemical diversity available. An existing peptide PS-SCL can be chemically transformed to generate a peptidomimetic SCL from which highly active individual compounds can be identified. The synthesis and deconvolution methods developed for peptide libraries are easily applied to other types of chemical pharmacophores. The soluble nature of the nonsupport-bound combinatorial libraries is a distinct advantage over other methods in that membrane-bound and whole cell assays can also be used. In addition, the deconvolution methods used allow the chemical structure of peptidic, peptidomimetic, and organic compounds to be determined based solely on the structural similarities of compounds within each active pool or sublibrary.

Screening for an Inhibitor of Bacterial RNAP:

One aspect of the invention provides high throughput screening of molecules specific to the bacterial RNAP target. This can be done in many different ways well known in the art. For example, this could be done by attaching bacterial RNAP to the bottom of the wells of a 96-well plate at an appropriate concentration by incubating the RNAP in the well overnight at 4° C. Alternatively, the wells are first coated with compositions of polylysine that facilitates the binding of the bacterial RNAP to the wells. Following attachment, samples from a library of test compounds (concentrations are determined by the compound being tested) are added (along with an appropriate binding buffer known in the art) to the wells and incubated for a sufficient time and temperature to facilitate binding. Following the incubation, the wells are washed with an appropriate washing solution at 4° C. Increasing or decreasing salt and/or detergent concentrations in the wash varies the stringency of the washing steps. Detection of binding is accomplished using antibodies (representative examples include RIA and ELISA), biotinylation, biotin-streptavidin binding, and radioisotopes. The concentration of the sample library compounds is also varied to calculate a binding affinity by Scatchard analysis. Binding to the bacterial RNAP target identifies a "lead compound". Once a lead compound is identified, the screening process is repeated using compounds chemically related to the lead compound to identify compounds with the tightest binding affinities. Selected compounds having binding affinity are further tested in one of two assays. These assays use test compounds from 1) phage-displayed linear and cyclic decapeptide libraries and 2) iterative deconvolution of solution-phase linear and cyclic D-hexapeptide libraries.

A phage library can be used to test compounds that could bind to the RNA-exit-channel of bacterial RNAP. The phage library is constructed in the N-terminal region of the major coat protein pVIII, as previously described (Felici et al., 1991). In addition, in an attempt to define a more constrained context, two Cys are included as invariant residues flanking the random nonapeptide. Transformation yields approximately $1 \times 10^8$ independent clones, and the presence of a productive insert is indicated by the blue color of the colonies on Xgal/IPTG plates (Felici et al., 1991). The construction of the library results in hybrid capsids, expressing the random peptides, dispersed along wild type pVIII copies. The absence of the Cys in wild type pVIII allows one to detect the presence of free thiol groups in the hybrid capsids. Clones are analyzed with a Cys-specific compound (e.g., DIG protein detection kit, Boehringer Mannheim, Germany) in order to show some of the peptides are in cyclized form. This indicates that in many cases the insert is displayed as a loop structure, which limits its mobility. Phage affinity purification is performed utilizing the biopanning technique, as previously described by Parmley and Smith (1988). After the round of biopanning, $10^4$ phage out of the initial $10^{10}$ are eluted from a streptavidin-coated plate. The phage is screened directly with a plaque assay. Single plaques ($10^5$) are transferred onto nitrocellulose and probed with RNAP. Positive plaques are eluted from nitrocellulose, the phage are amplified and sequenced, and their reactivity is further confirmed by dot-blot analysis. The amino acid sequences are then deduced.

Biologically active compounds are selected from large populations of randomly generated sequences. Libraries are made up of six-residue peptide sequences with amidated carboxy-termini and either acetylated or non-acetylated amino-termini. The first two amino acids in each peptide chain are individually and specifically defined, while the last four amino acids consist of equimolar, or close to equimolar, mixtures of each of the 20 naturally occurring L-amino acids. The peptides in these libraries are generally represented as Ac—$O_1O_2$XXXX—$NH_2$ and $O_1O_2$XXXX—$NH_2$, where $O_1$ and $O_2$ are defined positions, which are represented by the single letters AA, AC, AD and so on up to and including YV, YW, YY, to reach a total of 400 ($20^2$) combinations, and each X position is represented by an equimolar mixture of the 20 natural amino acids (non-natural amino acids can be used as well). Four mixture positions (XXXX) result in a total of 160,000 ($20^4$) different combinations. Each of the 400 different peptide mixtures that make up each of the libraries thus consists of 160,000 individual hexamers. In total, 64,000,000 peptides are represented. The peptides are attached to a resin or alternatively cleaved from the resin, extracted and lyophilized before use. Each nonsupport-bound peptide mixture is typically used at a concentration of 1 mg/ml. Therefore, if one assumes that the average molecular weight of Ac—$O_1O_2$XXXX—$NH_a$ is 785, then a mixture of 160,000 peptides at a total final concentration of 1 mg/ml yields a concentration of every peptide within each mixture of 8 nM, sufficiently high for most biologically significant interactions if even a single peptide sequence is active. After the mixture of libraries is screened for binding to bacterial RNAP, the remaining mixture positions are defined through an iterative enhancement and selection process in order to identify the most active sequence.

A rapid alternative method for identifying active compounds is the positional scanning approach. In this approach, if one uses a library made up of peptides, for example, each of the individual sub-libraries (one for each position along the peptide) that make up the positional scanning library is composed of 20 different peptide mixtures. Each position is defined (represented as 0) and occupied by one of the 20 natural L-amino acids; the remaining five positions of the six-residue sequence are composed of mixtures (represented as X) of the same 20 amino acids. The six different sub-libraries vary only in the location of their defined amino acids; they can therefore be represented as: Ac—$O_1$XXXXX—$NH_2$, Ac—X$O_2$XXXX—$NH_2$, Ac—XX$O_3$XXX—$NH_2$, Ac—XXX$O_4$XX—$NH_2$, AC-XXXX$O_5$X—$NH_2$, and Ac—XXXXX$O_6$—$NH_2$. Each individual peptide mixture, contains 3,200,000 ($20^5$) different compounds; each of the six positional sub-libraries contains 64,000,000 ($20 \times 20^5$) different compounds; and the complete library contains 384,000,000 ($6 \times 20 \times 20^5$) different compounds. Alternatively, each of the six individual sub-libraries (for example, Ac—XXX$O_4$XX—$NH_5$) can be examined independently and moved forward in an interactive fashion.

The assay components and various formats that may be utilized are described in the subsections below.

Assay Components:

The bacterial RNAP, or RNAP fragment or derivative, containing the RNA-exit-channel, and an inhibitory compound specific to the RNA-exit-channel of RNAP binding partners used as components in the assay may be derived from natural sources (e.g., purified from bacterial RNAP using protein separation techniques well known in the art); produced by recombinant DNA technology using techniques known in the art (see, e.g., Sambrook et al., 1989, Molecular Cloning: A Laboratory Manual, Cold Spring Harbor Laboratories Press, Cold Spring Harbor, N.Y.); and/or chemically synthesized in whole or in part using techniques known in the art (see, e.g., Creighton, 1983, Proteins: Structures and Molecular Principles, W. H. Freeman & Co., N.Y., pp. 50-60). The composition of the synthetic peptides may be confirmed by amino acid analysis or sequencing; e.g., using the Edman degradation procedure (see, e.g., Creighton, 1983, supra at pp. 34-49).

One of the binding partners used in the assay system should be labeled, either directly or indirectly, to facilitate detection of a complex formed between the bacterial RNAP RNA-exit-channel and an inhibitory compound specific to the RNA-exit-channel of RNAP. Any of a variety of suitable labeling systems may be used including but not limited to radioisotopes such as $^{125}I$; enzyme labeling systems that generate a detectable colorimetric signal or light when exposed to substrate; and fluorescent labels.

Fluorescent labels are preferred.

Where recombinant DNA technology is used to produce the bacterial RNAP, RNAP fragment, or derivative containing the RNA exit channel, it may be advantageous to engineer fusion proteins that can facilitate labeling, immobilization and/or detection. For example, the coding sequence of the bacterial RNAP RNA-exit-channel can be fused to that of a heterologous protein that has enzyme activity or serves as an enzyme substrate in order to facilitate labeling and detection. The fusion constructs should be designed so that the heterologous component of the fusion product does not interfere with binding of the bacterial RNAP RNA-exit-channel and an inhibitory compound specific to the RNA-exit-channel of RNAP.

Indirect labeling involves the use of a third protein, such as a labeled antibody, which specifically binds to the bacterial RNAP RNA-exit-channel. Such antibodies include but are not limited to, polyclonal, monoclonal, chimeric, humanized, single chain, Fab fragments and fragments produced by an Fab expression library.

For the production of antibodies, various host animals may be immunized by injection with the bacterial RNAP RNA exit channel. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Monoclonal antibodies may be prepared by using any technique that provides for the production of antibody molecules by continuous cell lines in culture. These include, but are not limited to the hybridoma technique originally described by Kohler and Milstein, (Nature, 1975, 256:495-497), the human B-cell hybridoma technique (Kosbor et al., 1983, Immunology Today, 4:72, Cote et al., 1983, Proc. Natl. Acad. Sci., 80:2026-2030) and the EBV-hybridoma technique (Cole et al., 1985, Monoclonal Antibodies and Cancer Therapy, Alan R. Liss, Inc., pp. 77-96). In addition, techniques developed for the production of "chimeric antibodies" (Morrison et al., 1984, Proc. Natl. Acad. Sci., 81:6851-6855; Neuberger et al., 1984, Nature, 312:604-608; Takeda et al., 1985, Nature, 314:452-454) by splicing the genes from a mouse antibody molecule of appropriate antigen specificity together with genes from a human antibody molecule of appropriate biological activity. Alternatively, techniques described for the production of single chain antibodies (e.g., U.S. Pat. No. 4,946,778) can be adapted to produce single chain antibodies specific to the bacterial RNAP RNA-exit-channel.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275-1281) to allow rapid and easy identification of monoclonal Fab fragments with the desired specificity.

The assay can be conducted in a heterogeneous or homogeneous format. A heterogeneous assay is an assay in which reaction results are monitored by separating and detecting at least one component during or following reaction. A homogeneous reaction is an assay in which reaction results are monitored without separation of components.

In either approach, the order of addition of reactants can be varied to obtain different information about the compounds being tested. For example, test compounds that interfere with the interaction between the binding partners, e.g., by competition, can be identified by conducting the reaction in the presence of the test substance—i.e., by adding the test substance to the reaction mixture prior to or simultaneously with the bacterial RNAP RNA-exit-channel and an inhibitory compound specific to the RNAP RNA-exit-channel. On the other hand, test compounds that disrupt preformed complexes, e.g., compounds with higher binding constants that displace one of the binding partners from the complex, can be tested by adding the test compound to the reaction mixture after a complex between the binding partners has been formed.

In one example of a heterogeneous assay system, one binding partner—e.g., either the bacterial RNAP RNA-exit-channel or an inhibitory compound specific to the RNAP RNA-exit-channel—is anchored onto a solid surface, and the other binding partner, which is not anchored, is labeled, either directly or indirectly. In practice, microtiter plates are conveniently utilized. The anchored species may be immobilized by non-covalent or covalent attachments. Alternatively, an immobilized antibody specific for the bacterial RNAP RNA-exit-channel may be used to anchor the bacterial RNAP RNA-exit-channel to the solid surface. The surfaces may be prepared in advance and stored.

In order to conduct the assay, the non-immobilized binding partner is added to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the binding partner was pre-labeled, the detection of label immobilized on the surface indicates that complexes were formed. Where the binding partner is not pre-labeled, an indirect label can be used to detect complexes anchored on the surface; e.g., using a labeled antibody specific for the binding partner (the antibody, in turn, may be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for an epitope on the bacterial RNAP RNA-exit-channel to anchor any complexes formed in solution. Again, depending upon the order of addition of reactants to the liquid phase, test compounds which inhibit complex or which disrupt preformed complexes can be identified.

In a preferred embodiment of the invention, a homogeneous assay can be used. In this approach, a preformed complex of the bacterial RNAP RNA-exit-channel and an inhibitory compound specific to the RNA-exit-channel of RNAP is prepared in which one of the binding partners is labeled, but the signal generated by the label is quenched due to complex formation (see, e.g., U.S. Pat. No. 4,109,496). The addition of a test substance that competes with and displaces one of the binding partners from the preformed complex will result in the generation of a signal above background. In this way, test substances, which disrupt the bacterial RNAP RNA-exit-channel and an inhibitory compound specific to the RNA-exit-channel of RNAP interaction can be identified.

One aspect of the invention provides fluorescence resonance energy transfer (FRET)-based homogeneous assays to provide probe-labeled derivatives of an inhibitory compound specific to the RNA-exit-channel of RNAP. (Förster, 1948; reviewed in Lilley and Wilson. 2000; Selvin, 2000; Mukhopadhyay et al., 2001; Mekler et al., 2002; Mukhopadhyay et al., 2004). FRET occurs in a system having a fluorescent probe serving as a donor and a second fluorescent probe serving as an acceptor, where the emission wavelength of the donor overlaps the excitation wavelength of the acceptor. In such a system, upon excitation of the donor with light of its excitation wavelength, energy can be transferred from the donor to the acceptor, resulting in excitation of the acceptor and omission at the acceptor's emission wavelength.

With commonly used fluorescent probes, FRET permits accurate determination of distances in the range of ~20 to ~100 Å. FRET permits accurate determination of distances up to more than one-half the diameter of a transcription complex (diameter ~150 Å; Zhang et al. 1999; Cramer et al., 2001; Gnatt et al., 2001).

A preferred assay involves monitoring of FRET between: a) one of a fluorescent probe or a chromophore incorporated into a bacterial RNAP, and b) one of a fluorescent probe or a chromophore incorporated into a bacterial a region 3.2.

An especially preferred assay involves monitoring of FRET between: a) a fluorescent probe incorporated at one of residue 1377 of *Escherichia coli* RNAP β' subunit or residue and residue 235 of *Escherichia coli* RNAP $\alpha^{II}$ subunit, and b) a fluorescent probe incorporated at one of residue 527 of *Escherichia coli* $\sigma^{70}$ or residue 537 of *Escherichia coli* $\sigma^{70}$.

Another especially preferred assay involves monitoring of FRET between: a) one of rifampicin or a rifampicin derivative in complex with *Escherichia coli* RNAP, and b) a fluorescent probe incorporated at one of residue 527 of *Escherichia coli* $\sigma^{70}$ or residue 537 of *Escherichia coli* $\sigma^{70}$.

Another preferred assay involves monitoring of FRET between: a) one of a fluorescent probe or a chromophore incorporated into a bacterial RNAP, and b) one of a fluorescent probe or a chromophore incorporated into a small molecule that binds within the RNAP RNA-exit-channel.

An especially preferred assay involves monitoring of FRET between: a) one of a fluorescent probe or a chromophore incorporated into between a fluorescent probe incorporated at one of residue 1377 of *Escherichia coli* RNAP β' subunit or residue and residue 235 of *Escherichia coli* RNAP $\sigma^{II}$ subunit, and b) one of a fluorescent probe or a chromophore incorporated into Lpm.

In accordance with the invention, a given compound found to inhibit one bacterium may be tested for general antibacterial activity against a wide range of different bacterial species. For example, and not by way of limitation, a compound that inhibits the interaction of *Escherichia coli* RNAP, or a RNAP fragment or derivative thereof containing the RNA-exit-channel, can be tested, according to the assays described infra, against *Bacillus subtilis*.

Animal Model Assays:

Any of the inhibitory compounds, which are identified in the foregoing assay systems, may be tested for antibacterial activity in any one of the various microbiological assays known to the skilled worker in the field of microbiology.

The most effective inhibitors of bacterial RNAP identified by the processes of the present invention can then be used for subsequent animal experiments. The ability of an inhibitor to prevent bacterial infection can be assayed in animal models that are natural hosts for bacteria. Such animals may include mammals such as pigs, dogs, ferrets, mice, monkeys, horses, and primates. As described in detail herein, such animal models can be used to determine the $LD_{50}$ and the $LD_{50}$ in animal subjects, and such data can be used to derive the therapeutic index for the inhibitor of the bacterial RNAP RNA-exit-channel/inhibitory compound specific to the RNA-exit-channel of RNAP interaction.

Pharmaceutical Preparations and Methods of Administration:

The identified compounds that inhibit bacterial replication can be administered to a patient at therapeutically effective doses to treat bacterial infection. A therapeutically effective dose refers to that amount of the compound sufficient to result in amelioration of symptoms of bacterial infection.

Toxicity and therapeutic efficacy of such compounds can be determined by standard pharmaceutical procedures in cell cultures or experimental animals for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of infection in order to minimize damage to uninfected cells and reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal infection, or a half-maximal inhibition) as determined in cell culture. Such information can be used to more accurately determine useful doses in humans. Levels in plasma may be measured, for example, by high performance liquid chromatography.

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

As used herein a "small molecule" is a compound that has a molecular weight of less than 15 kDa.

As used herein a "small organic molecule" is an organic compound [or organic compound complexed with an inorganic compound (e.g., metal)] that has a molecular weight of less than 3 kDa.

As used herein the term "about" preferably means within 10 to 15%, preferably within 5 to 10%. For example, an amino acid sequence that contains about 60 amino acid residues preferably contains between 51 to 69 amino acid residues, more preferably 57 to 63 amino acid residues.

As used herein the term "target" minimally comprises amino acid residues of a target set of residues corresponding to, and alignable with, either with residue 1256 of the β subunit and residues 249 and 337 of the β' subunit of RNAP from *Escherichia coli* or a set of residues corresponding to, and alignable with residue 1061 of the β subunit and residues 238 and 326 of the β' subunit of RNAP from *Bacillus subtilis*.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc) (Reeck et al., Cell, 50:667 (1987)).

Accordingly, the term "sequence similarity" in all its grammatical forms refers to the degree of identity or correspondence between nucleic acid or amino acid sequences of proteins that do not share a common evolutionary origin (see Reeck et al., 1987, supra). However, in common usage and in the instant application, the term "homologous," when modified with an adverb such as "highly," may refer to sequence similarity and not a common evolutionary origin.

Similarly, in a particular embodiment, two amino acid sequences are "substantially homologous" or "substantially similar" when greater than 25% of the amino acids are identical, or greater than about 50% are similar (functionally identical). Preferably, the similar or homologous sequences are identified by alignment using, for example, the GCG (Genetics Computer Group, Program Manual for the GCG Package, Version 7, Madison, Wis.) pileup program with the default parameters.

The term "corresponding to" is used herein to refer similar or homologous sequences, whether the exact position is identical or different from the molecule to which the similarity or homology is measured. Thus, the term "corresponding to" refers to the sequence similarity, and not the numbering of the amino acid residues or nucleotide bases.

The present invention contemplates isolation of nucleic acids encoding the target. The present invention further provides for subsequent modification of the nucleic acid to generate a fragment or modification of the target that will crystallize.

Protein-Structure-Based Design of Inhibitors of Bacterial RNAP:

Once the three-dimensional structure of a crystal comprising a bacterial RNAP target is determined, a potential modulator of the target can be examined through the use of computer modeling using a docking program such as GRAM, DOCK, or AUTODOCK (Dunbrack et al., Folding & Design, 2:27-42 (1997)), to identify potential modulators of the bacterial RNAP target. This procedure can include computer fitting of potential modulators to the bacterial RNAP target to ascertain how well the shape and the chemical structure of the potential modulator will bind to either the individual bound subunits or to the bacterial RNAP target (Bugg et al., Scientific American, December:92-98 (1993); West et al., TIPS, 16:67-74 (1995)). Computer programs can also be employed to estimate the attraction, repulsion, and steric hindrance of the subunits with a modulator/inhibitor (e.g., the bacterial RNAP target and a potential stabilizer).

Initially, compounds known to bind to the target—for example, an inhibitory compound specific to the RNA-exit-channel of RNAP—can be systematically modified by computer modeling programs until one or more promising potential analogs are identified. In addition, systematic modification of selected analogs can then be systematically modified by computer modeling programs until one or more potential analogs are identified. Such analysis has been shown to be effective in the development of HIV protease inhibitors (Lam et al., Science 263:380-384 (1994); Wlodawer et al., Ann. Rev. Biochem. 62:543-585 (1993); Appelt, Perspectives in Drug Discovery and Design 1:23-48 (1993); Erickson, Perspectives in Drug Discovery and Design 1:109-128 (1993)). Alternatively, a potential modulator is obtained by initially screening a random peptide library produced by recombinant bacteriophage (Scott and Smith, Science, 249:386-390 (1990); Cwirla et al., Proc. Natl. Acad. Sci., 87:6378-6382 (1990); Devlin et al., Science, 249:404-406 (1990)). A peptide selected in this manner would then be systematically modified by computer modeling programs as described above, and then treated analogously to a structural analog as described below.

Once a potential modulator/inhibitor is identified, it can be either selected from a library of chemicals as are commercially available from most large chemical companies including Merck, Glaxo Welcome, Bristol Meyers Squib, Monsanto/Searle, Eli Lilly, Novartis and Pharmacia UpJohn, or alternatively the potential modulator may be synthesized de novo. As mentioned above, the de novo synthesis of one, or even a group of, specific compounds is reasonable in the art of drug design. The potential modulator can be placed into a standard binding assay with RNAP or an active fragment thereof such as the target, for example. The subunit fragments can be synthesized by either standard peptide synthesis described above, or generated through recombinant DNA technology or classical proteolysis. Alternatively, the corresponding full-length proteins may be used in these assays.

For example, the bacterial RNAP target can be attached to a solid support. Methods for placing the bacterial RNAP target on the solid support are well known in the art and include such things as linking biotin to the target and linking avidin to the solid support. The solid support can be washed to remove unreacted species. A solution of a labeled potential modulator (e.g., an inhibitor) can be contacted with the solid support. The solid support is washed again to remove the potential modulator not bound to the support. The amount of labeled potential modulator remaining with the solid support and thereby bound to the bacterial RNAP target can be determined. Alternatively, or in addition, the dissociation constant between the labeled potential modulator and the bacterial RNAP target, for example can be determined. Suitable labels for bacterial RNAP target or the potential modulator are exemplified herein. In a particular embodiment, isothermal calorimetry can be used to determine the stability of the bacterial RNAP target in the absence and presence of the potential modulator.

In another aspect of the present invention, a compound is assayed for its ability to bind to the bacterial RNAP target. A compound that binds to the bacterial RNAP target then can be selected. In a particular embodiment, the effect of a potential modulator on an activity of the bacterial RNAP target is determined. The potential modulator then can be added to a bacterial culture to ascertain its effect on bacterial proliferation. A potential modulator that inhibits bacterial proliferation then can be selected.

In a particular embodiment, the effect of the potential modulator on an activity of a bacterial RNAP, or a fragment thereof, is determined (either independently, or subsequent to a binding assay as exemplified above). In one such embodiment, the extent or rate of the DNA-dependent RNA transcription is determined. For such assays, a labeled nucleotide could be used. This assay can be performed using a real-time assay, e.g., with a fluorescent analog of a nucleotide. Alternatively, the determination can include the withdrawal of aliquots from the incubation mixture at defined intervals and subsequent placing of the aliquots on nitrocellulose paper or on gels. In a particular embodiment, the potential modulator is selected when it is an inhibitor of the bacterial RNAP.

One assay for RNAP activity is a modification of the method of Burgess et al. (*J. Biol. Chem.*, 244:6160 (1969); see http://www.worthington-biochem.com/manual/R/RNAP.html). One unit incorporates one nanomole of UMP into acid insoluble products in 10 minutes at 37° C. under the assay conditions such as those listed below. The suggested recompounds are: (a) 0.04 M Tris-HCl, pH 7.9, containing 0.01 M $MgCl_2$, 0.15 M KCl, and 0.5 mg/ml BSA; (b) nucleoside triphosphates (NTP): 0.15 mM each of ATP, CTP, GTP, UTP; spiked with $^3$H-UTP 75000-150000 cpms/0.1 ml; (c) 0.15 mg/ml calf thymus DNA; (d) 10% cold perchloric acid; and (e) 1% cold perchloric acid. 0.1-0.5 units of RNAP in 5 μl-10 μl are used as the starting enzyme concentration.

The procedure is to add 0.1 ml Tris-HCl, 0.1 ml NTP and 0.1 ml DNA to a test tube for each sample or blank. At zero time enzyme (or buffer for blank) is added to each test tube, and the contents are then mixed and incubated at 37° C. for 10 minutes. 1 ml of 10% perchloric acid is added to the tubes to stop the reaction. The acid insoluble products can be collected by vacuum filtration through Millipore filter discs having a pore size of 0.45 u-10 u (or equivalent). The filters are then washed four times with 1% cold perchloric acid using 1 ml-3 ml for each wash. These filters are then placed in scintillation vials. Two ml of methyl cellosolve are added to the scintillation vials to dissolve the filters. When the filters are completely dissolved (after about five minutes) 10 ml of scintillation fluid are added and the vials are counted in a scintillation counter.

Additional assays for analysis of RNAP activity contemplated by the present invention include RNA transcription assays and fluorescence-detected abortive initiation assays, concerning defining the target of an inhibitory compound specific to the RNA-exit-channel of RNAP. The present invention further provides for assays for analysis of antibacterial activity, such as for example include a Minimal Bacteriocidal Concentration (MBC) assay, concerning defining the target of an inhibitory compound specific to the RNA-exit-channel of RNAP.

For calculation of units of RNAP/mg of protein the equation described in U.S. Pat. No. 6,225,076 can be used.

When suitable potential modulators are identified, a crystal can be grown that comprises the bacterial RNAP, or a fragment thereof, and the potential modulator. Preferably, the crystal effectively diffracts X-rays for the determination of the atomic coordinates of the protein-ligand complex to a resolution of better than 4.0 Å. The three-dimensional structure of the crystal is determined by molecular replacement. Molecular replacement involves using a known three-dimensional structure as a search model to determine the structure of a closely related molecule or protein-ligand complex in a new crystal form. The measured X-ray diffraction properties of the new crystal are compared with the search model structure to compute the position and orientation of the protein in the new crystal. Computer programs that can be used include: X-PLOR, CNS, (Crystallography and NMR System, a next level of XPLOR), and AMORE (J. Navaza, *Acta Crystallographics ASO*, 157-163 (1994)). Once the position and orientation are known, an electron density map can be calculated using the search model to provide X-ray phases. Thereafter, the electron density is inspected for structural differences and the search model is modified to conform to the new structure. Using this approach, it will be possible to solve the three-dimensional structure of different bacterial target having preascertained amino acid sequences. Other computer programs that can be used to solve the structures of the bacterial RNAP from other organisms include: QUANTA, CHARM; INSIGHT; SYBYL; MACROMODE; and ICM.

A candidate drug can be selected by performing rational drug design with the three-dimensional structure determined for the crystal, preferably in conjunction with computer modeling discussed above. The candidate drug (e.g., a potential modulator of bacterial RNAP) can then be assayed as exemplified above, or in situ. A candidate drug can be identified as a drug, for example, if it inhibits bacterial proliferation.

A potential inhibitor (e.g., a candidate antibacterial agent) would be expected to interfere with bacterial growth. Therefore, an assay that can measure bacterial growth may be used to identify a candidate antibacterial agent.

Methods of testing a potential bacteriostatic or bacteriocidal compound (e.g., the candidate antibacterial agent) in isolated cultures and in animal models are well known in the art, and can include standard minimum-inhibitory-concentration (MIC) and minimum-bacteriocidal-concentration (MBC) assays. In animal models, the potential modulators can be administered by a variety of ways including topically, orally, subcutaneously, or intraperitoneally depending on the proposed use. Generally, at least two groups of animals are used in the assay, with at least one group being a control group, which is administered the administration vehicle without the potential modulator.

For all of the assays described herein further refinements to the structure of the compound generally will be necessary and can be made by the successive iterations of any and/or all of the steps provided by the particular screening assay.

The present invention is not to be limited in scope by the specific embodiments describe herein. Indeed, various modifications of the invention in addition to those described herein will become apparent to those skilled in the art from the foregoing description and the accompanying figures. Such modifications are intended to fall within the scope of the appended claims.

EXAMPLES

The invention provides a target and methods for specific binding and inhibition of RNA polymerase from bacterial species. The invention has applications in control of bacterial gene expression, control of bacterial growth, antibacterial chemistry, and antibacterial therapy.

Example 1

The macrocyclic antibiotic lipiarmycin (Lpm) inhibits bacterial RNAP (Sergio et al., (1975) *J. Antibiot.* 1975, 543-549; Talpaert et al., (1975) *Biochem. Biophys. Res. Commun.* 63, 328-334; Sonenshein et al., (1977) *J. Bacteriol.* 132, 73-79; Sonenshein et al., (1979) *J. Mol. Biol.* 127, 55-72). Lpm-resistant (Lpm$^R$) mutants of *Bacillus subtilis* previously have been isolated and mapped to the locus encoding the RNAP β and β' subunits (Sonenshein et al., (1977) *J. Bacteriol.* 132, 73-79). Applicant has obtained and sequenced three such mutants (provided by L. Sonenshein, Tufts University Medical School). As shown in Table 1, applicant's sequencing data indicated that the first Lpm$^R$ isolate from *Bacillus subtilis* has a CAA to AAA codon substitution in the rpoB gene resulting in a Gln to Lys amino acid substitution at residue 1061. The second Lpm$^R$ isolate from *Bacillus subtilis* has a CTC to CGC codon substitution in the rpoC gene resulting in a Leu to Arg amino acid substitution at residue 238. The third Lice isolate from *Bacillus subtilis* has a CGC to CCC codon substitution in the rpoC gene resulting in an Arg to Cys amino acid substitution at residue 326. The corresponding amino acid residues of the *Escherichia coli* RNAP β and β' subunits are, respectively, 1256, 249, and 337. In the three-dimensional structure of bacterial RNAP (Zhang et al., (1999) *Cell* 98, 811-824; Murakami et al., (2002) *Science* 296, 1280-1284; Vassylyev et al., (2002) *Nature* 417, 712-719), these residues cluster tightly and are located in, or immediately adjacent to, the entrance to the RNA-exit-channel (FIG. 2).

TABLE 1

LPM$^R$ ISOLATES FROM BACILLUS SUBTILIS

| Allele | Gene | Amino acid substitution | Codon substitution |
|---|---|---|---|
| LS121 | rpoB | 1061 Gln→Lys | CAA→AAA |
| HA4 | rpoC | 238 Leu→Arg | CTC→CGC |
| LS105 | rpoC | 326 Arg→Cys | CGC→CCC |

Example 2

To define systematically determinants for function of Lpm, saturation mutagenesis of *Escherichia coli* rpoB and rpoC was performed, and Lpm$^R$ mutants were isolated and characterized (targeting codons for residues located within 20 Å of *Bacillus subtilis* Lpm$^R$ sites in the three-dimensional structure of RNAP; methods as in Mukhopadhyay, et al., (2004) *Mol. Cell*, in press, except that selection was performed in hyper-permeable strain D21f2/TolC (rfa tolC; Fralick et al., (1994) *J. Bacteriol.* 176, 6404-6406)). 24 independent single-substitution Lpm$^r$ mutants were identified (Table 2). The substitution sites define an approximately 20 Å×20 Å continuous surface, located within the RNA-exit-channel, spanning the target, and containing each residue of the target (i.e., residues 1251, 1256, and 1321 of β and residues 248-249 of β'; Table 2). Substitution sites corresponding to substitution sites in the *Bacillus subtilis* Lpm$^R$ mutants described above were among those identified (i.e., residue 1256 of and residues 249 and 337 of β'; Tables 1, 2).

TABLE 2

ESCHERICHIA COLI LPM$^R$ ISOLATES FROM SATURATION MUTAGENESIS AND SELECTION

| Amino acid substitution | Number of independent isolates | MIC (mg/ml) (wild-type = 1) |
|---|---|---|
| RpoB | | |
| 1251 Tyr→Phe | 3 | 10 |
| 1256 Gln→Glu | 2 | 10 |
| 1256 Gln→Leu | 1 | 5 |
| 1302 Thr→Pro | 1 | 5 |
| 1318 Gly→Ser | 1 | 5 |
| 1319 Met→Lys | 1 | 5 |
| 1319 Met→Arg | 2 | 10 |
| 1321 Glu→Val | 1 | 5 |
| 1325 Val→Leu | 1 | 5 |
| 1325 Val→Ala | 2 | 10 |
| RpoC | | |
| 248 Asp→Tyr | 1 | 5 |
| 249 Leu→Arg | 2 | 5 |
| 337 Arg→Ser | 3 | 5 |
| 337 Arg→Hys | 3 | 5 |

Example 3

Fluorescence-resonance-energy-transfer (FRET) was used to assess effects of Lpm on distances between fluorescent probes incorporated into bacterial REAP and complementary fluorescent probes incorporated into the bacterial initiation factor σ$^{70}$ in the context of RNAP holoenzyme (composition β'/β/α$^{II}$/ω/σ$^{70}$).

FRET occurs in a system having a fluorescent probe serving as a donor and a second fluorescent probe serving as an acceptor, where the emission wavelength of the donor overlaps the excitation wavelength of the acceptor. In such a system, upon excitation of the donor with light of its excitation wavelength, energy can be transferred from the donor to the acceptor, resulting in excitation of the acceptor and emission at the acceptor's emission wavelength. The efficiency of energy transfer, E, is a function of the Förster parameter, R$_o$, and of the distance between the donor and the acceptor, R:

$$E = [1+(R/R_o)^6]^{-1}$$

Thus, if one quantifies E and R$_o$, one can determine R. With commonly used fluorescent probes, FRET permits accurate determination of distances in the range of ~20 to ~100 Å. Thus, FRET permits accurate determination of distances up to more than one-half the diameter of a transcription complex (diameter ~150 Å; Zhang et al., 1999; Cramer et al., 2001; Gnatt et al., 2001).

Experiments were performed using methods as in Mekler et al., (2002) *Cell* 208, 599-614. The fluorescent probe fluorescein (F) was incorporated at each of two sites within the *Escherichia coli* RNAP core: residue 1377 of β' and residue 235 of α$^{II}$. The two probe sites are well separated in the structure of RNAP, are located at the periphery of the RNAP, and bracket the central portion of RNAP and the active-site cleft of RNAP. The positions of the probe sites permit accurate three-dimensional determination of the positions of the complementary probes in $\sigma^{70}$.

The fluorescent probe tetramethylrhodamine (TMR) was incorporated at each of eleven sites within *Escherichia coli* $\sigma^{70}$, including sites within σ region 1.1 (residue 59), σ region 2 (residue 366), σ region 3.1 (residue 459), σ region 3.2 (residues 517, 527, and 537), and a region 4 (residues 560, 569, 578, 583, and 596).

For each combination of probe-labeled RNAP core derivative and probe-labeled a derivative, RNAP holoenzyme was prepared and probe-probe distances were determined using FRET (Tables 3A, 3B). The results establish that binding of Lpm to RNAP results in a dramatic change in the position of a region 3.2, corresponding to displacement of a region 3.2 from the RNA-exit-channel (>>10 Å decrease in distance between β' residue 1377 and σ residues 527 and 537; >>10 Å decrease in distance between α$^{II}$ residue 235 and σ residues 527 and 537; Tables 3A, 3B). The effect is specific to σ region 3.2. Thus, no significant changes in probe-probe distance are observed for probes in a regions 1.1, 2, 3.1, and 4.

TABLE 3A

FRET: β'1377-F/σ-TMR

| σ region | σ residue | R (Å) –Lpm | R (Å) +Lpm |
|---|---|---|---|
| σ R1.1 | 59 | 74 | 74 |
| σ R2 | 366 | 74 | 74 |
| σ R3.1 | 459 | 68 | 66 |
| σ R3.2 | 517 | 63 | 60 |
|  | 527 | <u>72</u> | <u>62</u> |
|  | 537 | <u>73</u> | <u>58</u> |
| σ R4 | 560 | 72 | 72 |
|  | 569 | 66 | 66 |
|  | 578 | 73 | 72 |
|  | 583 | 79 | 80 |
|  | 596 | 68 | 69 |

TABLE 3B

FRET: α''235-F/σ-TMR

| σ region | σ residue | R (Å) –Lpm | R (Å) +Lpm |
|---|---|---|---|
| σ R1.1 | 59 | 111 | 111 |
| σ R2 | 366 | 125 | 125 |
| σ R3.1 | 459 | 94 | 94 |
| σ R3.2 | 517 | 74 | 73 |
|  | 527 | <u>84</u> | <u>74</u> |
|  | 537 | <u>84</u> | <u>75</u> |
| σ R4 | 560 | 95 | 95 |
|  | 569 | 95 | 95 |
|  | 578 | 104 | 104 |
|  | 583 | 99 | 99 |
|  | 596 | 75 | 75 |

Example 4

To determine whether Lpm inhibits steps in transcription up to and including formation of the RNAP-promoter open complex, electrophoretic mobility-shift experiments were performed. The analysis of open-complex formation was performed as follows: reaction mixtures (20 nl) contained 100 nM RNAP holoenzyme, 20 nM fluorochrome-labeled DNA fragment lacUVS-12(Cy5, +26) (Mukhopadhyay et al., 2001), and 0-100 μM Lpm in TB (50 mM Tris-HCl (pH 8.0), 100 mM KCl, 10 mM MgCl$_2$, 1 mM dithiothreitol, 10 μg/ml bovine serum albumin, and 5% glycerol), added before or after the DNA. Following 15 min at 37° C., 0.5 μl 1 mg/ml heparin was added (to disrupt non-specific complexes), and, following a further 2 minutes at 37° C., reaction mixtures were applied to 5% polyacrylamide slab gels (30:1 acrylamide/bisacrylamide; 6×9×0.1 cm) and electrophoresed in 90 mM Tris-borate (pH 8.0) and 0.2 mM EDTA (20 V/cm; 30 min at 37° C.) and analyzed using a fluorescence scanner (Storm 860; Molecular Dynamics).

Figure 3:
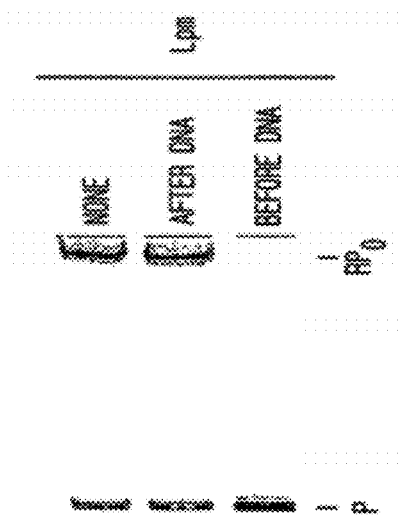
FIG. 3 shows a polyacrylamide gel illustrating Lpm inhibition of formation of RNAP-promoter open complex.

The results establish that Lpm inhibits formation of the RNAP-promoter open complex when added to RNAP before addition of the promoter DNA (FIG. 3).

INDUSTRIAL APPLICABILITY

Compounds identified according to the target and method of this invention would have applications not only in antibacterial therapy, but also in (a) identification of bacterial RNAP (diagnostics, environmental-monitoring, and sensors applications), (b) labeling of bacterial RNAP (diagnostics, environmental-monitoring, imaging, and sensors applications), (c) immobilization of bacterial RNAP (diagnostics, environmental-monitoring, and sensors applications), (d) purification of bacterial RNA polymerase (biotechnology applications), (e) regulation of bacterial gene expression (biotechnology applications), and (f) antisepsis (antiseptics, disinfectants, and advanced-materials applications).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

All patent and non-patent publications cited in this specification are indicative of the level of skill of those skilled in the art to which this invention pertains. All these publications and patent applications are herein incorporated by reference to the same extent as if each individual publication or patent application was specifically and individually indicated to be incorporated herein by reference.

The invention claimed is:

1. A method for identifying an agent that inhibits an activity of a bacterial RNAP by binding to a homologous RNA-exit-channel amino-acid sequence of a bacterial RNAP, comprising: (a) preparing a reaction solution comprising the agent to be tested and a bacterial RNAP that contains a homologous RNA-exit-channel amino-acid sequence; (b) detecting at least one of the presence, extent, concentration-dependence, or kinetics of inhibition of an activity of said bacterial RNAP in the reaction solution, by binding of the agent to the homologous RNA-exit-channel amino-acid sequence of the bacterial RNAP; (c) using the information obtained in step (b) to identify one or more agents that inhibit an activity of the bacterial RNAP by binding to the homologous RNA-exit channel amino-acid sequence of the bacterial RNAP, wherein the agent is not lipiarmycin.

2. The method of claim 1 wherein the bacterial RNAP in the reaction solution is an intact bacterial RNAP.

3. The method of claim 1 wherein bacterial RNAP in the reaction solution is *Escherichia coli* RNAP or a derivative thereof.

4. The method of claim 1 wherein the bacterial RNAP in the reaction solution is *Bacillus subtilis* RNAP or a derivative thereof.

5. The method of claim 1 wherein the activity is transcription initiation.

6. The method of claim 1 wherein the activity is transcription elongation.

7. The method of claim 1 wherein the activity is a binding.

8. The method of claim 1 wherein the activity is NTP binding.

9. The method of claim 1 wherein the activity is DNA binding.

10. The method of claim 1 wherein the activity is RNA binding.

11. The method of claim 1 wherein the activity is open-complex formation.

12. The method of claim 1 wherein the activity is RNA synthesis.

13. The method of claim 1 further comprising the step of: detecting at least one of the presence, extent, concentration-dependence, or kinetics of the inhibition by the agent of the activity of a second entity that contains a derivative of a bacterial RNAP homologous RNA-exit-channel amino-acid sequence having at least one substitution, insertion, or deletion.

14. The method of claim 13 wherein the second entity is a derivative of an intact bacterial RNAP.

15. The method of claim 13 wherein the second entity is a derivative of a fragment of a bacterial RNAP.

16. The method of claim 13 wherein the second entity is *Escherichia coli* RNAP or a derivative thereof.

17. The method of claim 13 wherein the second entity is *Bacillus subtilis* RNAP or a derivative thereof.

18. The method of claim 13 wherein the activity is transcription initiation.

19. The method of claim 13 wherein the activity is transcription elongation.

20. The method of claim 13 wherein the activity is open-complex formation.

21. The method of claim 13 wherein the activity is NTP binding.

22. The method of claim 13 wherein the activity is DNA binding.

23. The method of claim 13 wherein the activity is RNA binding.

24. The method of claim 13 wherein the activity is open-complex formation.

25. The method of claim 13 wherein the activity is RNA synthesis.

26. The method of claim 13 wherein inhibition of an activity of the bacterial RNAP in the reaction solution and inhibition of an activity of the second entity are assessed sequentially.

27. The method of claim 13 wherein inhibition of an activity of the bacterial RNAP in the reaction solution and inhibition of an activity of the second entity are assessed simultaneously.

28. The method of claim 1 further comprising comparison of: (a) at least one of the presence, extent, concentration-dependence, or kinetics of inhibition by the agent of an activity of the bacterial RNAP in the reaction solution, and (b) at least one of the presence, extent, concentration-dependence, or kinetics of inhibition by the agent of an activity of a eukaryotic RNAP derivative.

29. The method of claim 28 wherein the eukaryotic RNAP derivative is a human RNAP derivative.

30. The method of claim 28 wherein the eukaryotic RNAP derivative is a human RNAP II derivative.

31. The method of claim 1 wherein at least one of the presence, extent, concentration-dependence, or kinetics of inhibition by the agent of an activity of the bacterial RNAP in the reaction solution also is compared to at least one of the presence, extent, concentration-dependence, or kinetics of inhibition by lipiarmycin.

* * * * *